(12) United States Patent
Kister et al.

(10) Patent No.: US 11,718,604 B2
(45) Date of Patent: Aug. 8, 2023

(54) 4-AMINO-6-(1,3-BENZODIOXOLE) PICOLINATES AND THEIR USE AS HERBICIDES

(71) Applicant: Dow AgroSciences LLC, Indianapolis, IN (US)

(72) Inventors: Jeremy Kister, Carmel, IN (US); Norbert M. Satchivi, Carmel, IN (US); Thomas L. Siddall, Zionsville, IN (US); Lindsey G. Horty, Indianapolis, IN (US); Noormohamed M. Niyaz, Indianapolis, IN (US); Jeffrey B. Epp, Noblesville, IN (US)

(73) Assignee: DOW AGROSCIENCES LLC

( * ) Notice: Subject to any disclaimer, the term of this patent is extended or adjusted under 35 U.S.C. 154(b) by 138 days.

(21) Appl. No.: 17/052,939

(22) PCT Filed: May 9, 2019

(86) PCT No.: PCT/US2019/031428
§ 371 (c)(1),
(2) Date: Nov. 4, 2020

(87) PCT Pub. No.: WO2019/217617
PCT Pub. Date: Nov. 14, 2019

(65) Prior Publication Data
US 2021/0230147 A1 Jul. 29, 2021

Related U.S. Application Data

(60) Provisional application No. 62/670,538, filed on May 11, 2018.

(51) Int. Cl.
| | | |
|---|---|---|
| C07D 405/04 | (2006.01) | |
| A01N 25/32 | (2006.01) | |
| A01N 43/40 | (2006.01) | |
| A01N 43/90 | (2006.01) | |

(52) U.S. Cl.
CPC .......... *C07D 405/04* (2013.01); *A01N 25/32* (2013.01); *A01N 43/40* (2013.01)

(58) Field of Classification Search
None
See application file for complete search history.

(56) References Cited

U.S. PATENT DOCUMENTS

| | | | | |
|---|---|---|---|---|
| 8,449,917 | B2 * | 5/2013 | Dave | A01N 25/12 |
| | | | | 504/307 |
| 9,149,038 | B2 * | 10/2015 | Eckelbarger | A01N 43/40 |
| 2003/0114311 | A1 | 6/2003 | Balko et al. | |
| 2012/0071320 | A1 * | 3/2012 | Atkinson | A01N 25/04 |
| | | | | 504/354 |
| 2012/0157314 | A1 | 6/2012 | Ahrens et al. | |
| 2014/0274701 | A1 | 9/2014 | Eckelbarger et al. | |
| 2015/0051074 | A1 | 2/2015 | Rosinger et al. | |
| 2015/0351396 | A1 * | 12/2015 | Hercamp | A01N 43/54 |
| | | | | 504/105 |
| 2015/0351398 | A1 * | 12/2015 | Hercamp | A01N 43/90 |
| | | | | 504/105 |

OTHER PUBLICATIONS

PUBCHEM, CID 90437806, 4-Amino-3-chloro-6-(2,2-difluoro-1,3-benzodioxol-4-yl)-5-fluoropyridine-2-carboxylic acid, https://pubchem.ncbi.nlm.nih.gov/compound/90437306, downloaded Oct 29, 2020. PUBCHEM CID 90437806, pp. 1-7, Create Date; Feb. 13, 2015; p. 2, see 2D structure.
PCT/US19/31428, International Search Report and Written Opinion, dated Jul. 19, 2019.
EP19800736.1, European Supplemental Search and Written Opinion, dated Dec. 9, 2021.

* cited by examiner

*Primary Examiner* — Alton N Pryor

(57) ABSTRACT

Described herein are 4-amino-6-(1,3-benzodioxole)picolinic acids, compositions comprising 4-amino-6-(1,3-benzodioxole)picolinic acids, and the use of these compounds and compositions to control undesirable vegetation.

20 Claims, 8 Drawing Sheets

4-AMINO-6-(1,3-BENZODIOXOLE) PICOLINATES AND THEIR USE AS HERBICIDES

CROSS-REFERENCE TO RELATED APPLICATIONS

This application is the U.S. national stage entry of the International Application No. PCT/US2019/031428, filed May 9, 2019, which claims the benefit of priority to U.S. Provisional Application No. 62/670,538, filed May 11, 2018, the contents of which are hereby incorporated herein by reference in their entirety.

BACKGROUND

The occurrence of undesirable vegetation, e.g., weeds, is a constant problem facing farmers in crops, pasture, and other settings. Weeds compete with crops and negatively impact crop yield. The use of chemical herbicides is an important tool in controlling undesirable vegetation.

There remains a need for new chemical herbicides that offer a broader spectrum of weed control, selectivity, minimal crop damage, storage stability, ease of handling, higher activity against weeds, and/or a means to address herbicide-tolerance that develops with respect to herbicides currently in use. The compounds, compositions, and methods discussed herein address these and other needs.

SUMMARY

Provided herein are compounds defined by Formula I

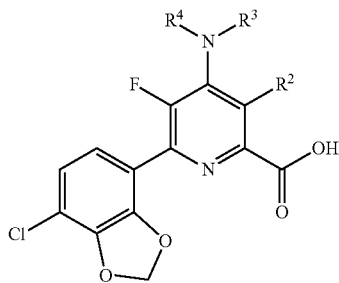

(I)

wherein $R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^5$=$CR^6$—$SiR^7R^8R^9$, wherein $R^5$ is hydrogen, F, or Cl; $R^6$ is hydrogen, F, Cl, $C_1$-$C_4$ alkyl, or $C_1$-$C_4$ haloalkyl; and $R^7$, $R^8$, and $R^9$ are independently $C_1$-$C_{10}$ alkyl, $C_3$-$C_6$ cycloalkyl, phenyl, substituted phenyl, $C_1$-$C_{10}$ alkoxy, or OH; and $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$ ($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

or an agriculturally acceptable salt, ester, or N-oxide thereof.

In some embodiments, the compound can be defined by Formula IA:

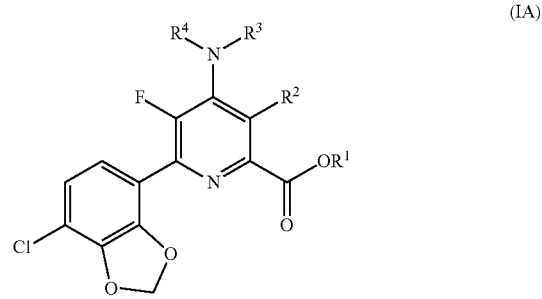

(IA)

wherein $R^1$ is hydrogen, $C_1$-$C_8$ alkyl, $C_1$-$C_8$ haloalkyl, $C_2$-$C_8$ alkenyl, $C_2$-$C_8$ haloalkenyl, $C_2$-$C_8$ alkynyl, phenyl, substituted phenyl, or $C_7$-$C_{12}$ arylalkyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^5$=$CR^6$—$SiR^7R^8R^9$, wherein $R^5$ is hydrogen, F, or Cl; $R^6$ is hydrogen, F, Cl, $C_1$-$C_4$ alkyl, or $C_1$-$C_4$ haloalkyl; and $R^7$, $R^8$, and $R^9$ are independently $C_1$-$C_{10}$ alkyl, $C_3$-$C_6$ cycloalkyl, phenyl, substituted phenyl, $C_1$-$C_{10}$ alkoxy, or OH; and $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$ ($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

or an agriculturally acceptable salt or N-oxide thereof.

Also provided are herbicidal compositions comprising a compound of Formula I and/or Formula IA and an agriculturally acceptable adjuvant or carrier.

Also provided are methods for controlling undesirable vegetation that comprise applying a herbicidally effective amount of a compound of Formula I and/or Formula IA or a herbicidal composition comprising a compound of Formula I and/or Formula IA and an agriculturally acceptable adjuvant or carrier.

DETAILED DESCRIPTION

Definitions

Figure 1A:
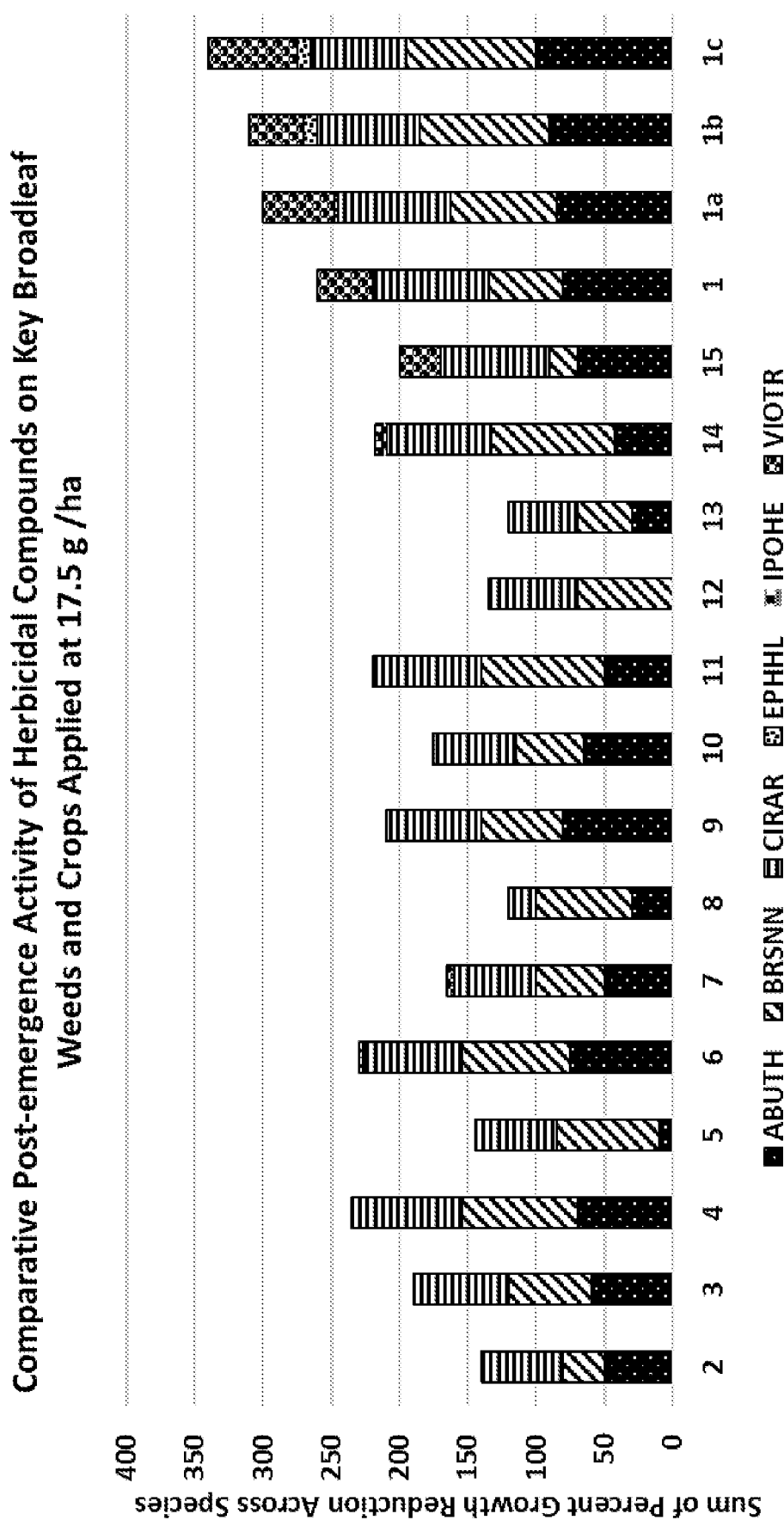
FIG. 1A is a plot of the activity of Compounds 1-15 against selected broadleaf weed species at an application rate of 17.5 g ai/ha.

As used herein, herbicide and herbicidal active ingredient mean a compound that controls undesirable vegetation when applied in an appropriate amount.

As used herein, control of or controlling undesirable vegetation means killing or preventing the vegetation, or causing some other adversely modifying effect to the vegetation e.g., deviations from natural growth or development, regulation, desiccation, retardation, and the like.

As used herein, a herbicidally effective or vegetation controlling amount is an amount of herbicidal active ingredient the application of which controls the relevant undesirable vegetation.

As used herein, applying a herbicide or herbicidal composition means delivering it directly to the targeted vegetation or to the locus thereof or to the area where control of undesired vegetation is desired. Methods of application include, but are not limited to pre-emergently contacting soil or water, post-emergently contacting the undesirable vegetation or area adjacent to the undesirable vegetation.

As used herein, plants and vegetation include, but are not limited to, dormant seeds, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending on the pH, may be in the dissociated or undissociated form.

Suitable salts include those derived from alkali or alkaline earth metals and those derived from ammonia and amines. Preferred cations include sodium, potassium, magnesium, and ammonium cations of the formula:

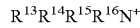

wherein $R^{13}$, $R^{14}$, $R^{15}$ and $R^{16}$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^{13}$, $R^{14}$, $R^{15}$ and $R^{16}$ are sterically compatible. Additionally, any two $R^{13}$, $R^{14}$, $R^{15}$ and $R^{16}$ together may represent an aliphatic difunctional moiety containing one to twelve carbon atoms and up to two oxygen or sulfur atoms. Salts of the compounds of Formula (I) can be prepared by treatment of compounds of Formula (I) with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide. In certain examples, amine salts can be preferred forms of the compounds of Formula (I) because they are water-soluble and lend themselves to the preparation of aqueous based herbicidal compositions, which can be desirable for certain applications.

Compounds of the Formula (I) include N-oxides. Pyridine N-oxides can be obtained by oxidation of the corresponding pyridines. Suitable oxidation methods are described, for example, in Houben-Weyl, *Methoden der organischen Chemie* [*Methods in organic chemistry*], expanded and subsequent volumes to the 4th edition, volume E 7b, p. 565 f.

As used herein, unless otherwise specified, acyl refers to formyl, $C_1$-$C_3$ alkylcarbonyl, and $C_1$-$C_3$ haloalkylcarbonyl. $C_1$-$C_6$ acyl refers to formyl, $C_1$-$C_5$ alkylcarbonyl, and $C_1$-$C_5$ haloalkylcarbonyl (the group contains a total of 1 to 6 carbon atoms).

As used herein, alkyl refers to saturated, straight-chained or branched saturated hydrocarbon moieties. Unless otherwise specified, $C_1$-$C_{10}$ alkyl groups are intended. Examples include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl.

As used herein, "haloalkyl" refers to straight-chained or branched alkyl groups, where in these groups the hydrogen atoms may partially or entirely be substituted with halogen atoms. Unless otherwise specified, $C_1$-$C_8$ groups are intended. Examples include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl, and 1,1,1-trifluoroprop-2-yl.

As used herein, alkenyl refers to unsaturated, straight-chained, or branched hydrocarbon moieties containing a double bond. Unless otherwise specified, $C_2$-$C_8$ alkenyl are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1- pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. Vinyl refers to a group having the structure —CH=CH$_2$; 1-propenyl refers to a group with the structure -CH=CH—CH$_3$; and 2-propenyl refers to a group with the structure —CH$_2$—CH=CH$_2$.

As used herein, alkynyl represents straight-chained or branched hydrocarbon moieties containing a triple bond. Unless otherwise specified, $C_2$-$C_8$ alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl.

As used herein, alkoxy refers to a group of the formula R—O—, where R is alkyl as defined above. Unless otherwise specified, alkoxy groups wherein R is a $C_1$-$C_8$ alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-dimethyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, haloalkoxy refers to a group of the formula R—O—, where R is haloalkyl as defined above. Unless otherwise specified, haloalkoxy groups wherein R is a $C_1$-$C_8$ alkyl group are intended. Examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2-difluoroethoxy, 2,2-dichloro-2-fluoroethoxy, 2,2,2-trichloroethoxy, pentafluoroethoxy, and 1,1,1-trifluoroprop-2-oxy.

As used herein, alkylthio refers to a group of the formula R—S— where R is alkyl as defined above. Unless otherwise specified, alkylthio groups wherein R is a $C_1$-$C_8$ alkyl group are intended. Examples include methylthio, ethylthio, propylthio, 1-methylethylthio, butylthio, 1-methyl-propylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, and 1-ethyl-2-methylpropylthio.

As used herein, haloalkylthio refers to an alkylthio group as defined above wherein the carbon atoms are partially or entirely substituted with halogen atoms. Unless otherwise specified, haloalkylthio groups wherein R is a $C_1$-$C_8$ alkyl group are intended. Examples include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio, and 1,1,1-trifluoroprop-2-ylthio.

As used herein, aryl, as well as derivative terms such as aryloxy, refers to a phenyl, indanyl or naphthyl group with phenyl being preferred. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more substituents selected from halogen, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_6$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_2$ alkyl and $C_1$-$C_2$ haloalkyl.

As used herein alkylcarbonyl refers to an alkyl group bonded to a carbonyl group. $C_1$-$C_3$ alkylcarbonyl and $C_1$-$C_3$ haloalkylcarbonyl refer to groups wherein a $C_1$-$C_3$ alkyl group is bonded to a carbonyl group (the group contains a total of 2 to 4 carbon atoms).

As used herein, alkoxycarbonyl refers to a group of the formula

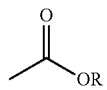

wherein R is alkyl.

As used herein, arylalkyl refers to an alkyl group substituted with an aryl group. $C_7$-$C_{10}$ arylalkyl refers to a group wherein the total number of carbon atoms in the group is 7 to 10.

As used herein alkylamino refers to an amino group substituted with one or two alkyl groups, which may be the same or different.

As used herein haloalkylamino refers to an alkylamino group wherein the alkyl carbon atoms are partially or entirely substituted with halogen atoms.

As used herein, $C_1$-$C_6$ alkylaminocarbonyl refers to a group of the formula RNHC(O)— wherein R is $C_1$-$C_6$ alkyl, and $C_1$-$C_6$ dialkylaminocarbonyl refers to a group of the formula $R_2$NC(O)— wherein each R is independently $C_1$-$C_6$ alkyl.

As used herein alkylcarbamyl refers to a carbamyl group substituted on the nitrogen with an alkyl group.

As used herein alkylsulfonyl refers to a group of the formula

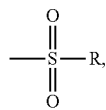

where R is alkyl.

As used herein carbamyl (also referred to as carbamoyl and aminocarbonyl) refers to a group of the formula

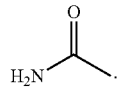

As used herein dialkylphosphonyl refers to a group of the formula

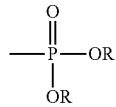

where R is independently alkyl in each occurrence.

As used herein, $C_1$-$C_6$ trialkylsilyl refers to a group of the formula —$SiR_3$ wherein each R is independently a $C_1$-$C_6$ alkyl group (the group contains a total of 3 to 18 carbon atoms).

As used herein Me refers to a methyl group; OMe refers to a methoxy group; i-Pr refers to an isopropyl group.

As used herein, the term "halogen" including derivative terms such as "halo" refers to fluorine, chlorine, bromine and iodine.

As used herein, plants and vegetation include, but are not limited to, germinant seeds, emerging seedlings, plants emerging from vegetative propagules, immature vegetation, and established vegetation.

Compounds

Provided herein are compounds of Formula I

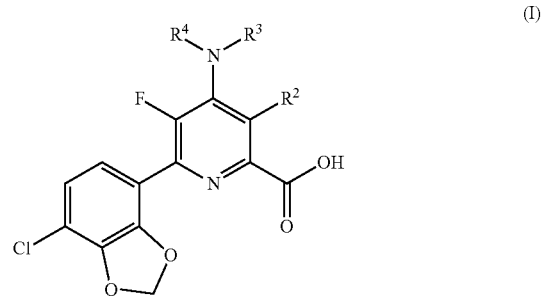

wherein $R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^5$=$CR^6$—$SiR^7R^8R^9$, wherein $R^5$ is hydrogen, F, or Cl; $R^6$ is hydrogen, F, Cl, $C_1$-$C_4$ alkyl, or $C_1$-$C_4$ haloalkyl; and $R^7$, $R^8$, and $R^9$ are independently $C_1$-$C_{10}$ alkyl, $C_3$-$C_6$ cycloalkyl, phenyl, substituted phenyl, $C_1$-$C_{10}$ alkoxy, or OH; and $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

as well as agriculturally acceptable salts, esters, and N-oxides thereof.

In some embodiments, the compound is the carboxylic acid or an agriculturally acceptable ester or salt. In some embodiments, the compound is the carboxylic acid or an agriculturally acceptable ester. In certain embodiments, the compound is the carboxylic acid. In certain embodiments, the compound can be an agriculturally acceptable ester (e.g., a methyl ester, a benzyl ester, or a propargyl ester).

In some embodiments, the compound can be defined by Formula IA:

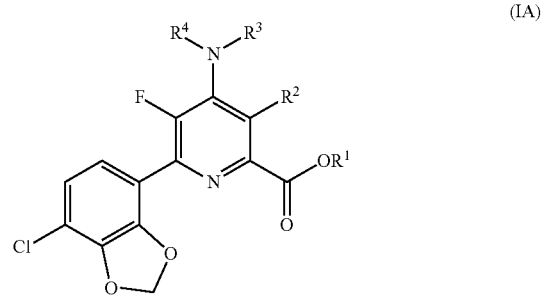

wherein

R¹ is hydrogen, $C_1$-$C_8$ alkyl, $C_1$-$C_8$ haloalkyl, $C_2$-$C_8$ alkenyl, $C_2$-$C_8$ haloalkenyl, $C_2$-$C_8$ alkynyl, phenyl, substituted phenyl, or $C_7$-$C_{12}$ arylalkyl;

R² is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —CR⁵=CR⁶—SiR⁷R⁸R⁹, wherein R⁵ is hydrogen, F, or Cl; R⁶ is hydrogen, F, Cl, $C_1$-$C_4$ alkyl, or $C_1$-$C_4$ haloalkyl; and R⁷, R⁸, and R⁹ are independently $C_1$-$C_{10}$ alkyl, $C_3$-$C_6$ cycloalkyl, phenyl, substituted phenyl, $C_1$-$C_{10}$ alkoxy, or OH; and R³ and R⁴ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or R³ and R⁴ taken together with N is a 5- or 6-membered saturated ring, or R³ and R⁴ taken together represent =CR³'(R⁴'), wherein R³' and R⁴' are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, R³' and R⁴' taken together with =C represent a 5- or 6-membered saturated ring;

or an agriculturally acceptable salt or N-oxide thereof.

In some embodiments of Formula IA, R¹ is hydrogen, $C_1$-$C_8$ alkyl, $C_2$-$C_8$ alkynyl, or $C_7$-$C_{10}$ arylalkyl. In some embodiments of Formula IA, R¹ is hydrogen. In some embodiments of Formula IA, R¹ is $C_1$-$C_8$ alkyl (e.g., a methyl group). In some embodiments of Formula IA, R¹ is $C_2$-$C_8$ alkynyl (e.g., a propargyl group). In some embodiments of Formula IA, R¹ is $C_7$-$C_{10}$ arylalkyl (e.g., a benzyl group).

In some embodiments of Formula I and/or Formula IA, R² is halogen, $C_2$-$C_4$-alkenyl, $C_2$-$C_4$-haloalkenyl, or $C_1$-$C_4$-alkoxy. In some embodiments of Formula I and/or Formula IA, R² is halogen, $C_2$-$C_4$-alkenyl, or $C_1$-$C_4$-alkoxy. In some embodiments of Formula I and/or Formula IA, R² is Cl, OMe, vinyl, or 1-propenyl. In some embodiments of Formula I and/or Formula IA, R² is Cl. In some embodiments of Formula I and/or Formula IA, R² is OMe. In some embodiments of Formula I and/or Formula IA, R² is vinyl or 1-propenyl.

In some embodiments of Formula I and/or Formula IA, R³ and R⁴ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, or R³ and R⁴ taken together represent =CR³'(R⁴'), wherein R³' and R⁴' are independently hydrogen, $C_1$-$C_6$ alkyl, $C_3$-$C_6$ alkenyl, $C_3$-$C_6$ alkynyl, $C_1$-$C_6$ alkoxy, or $C_1$-$C_6$ alkylamino. In some embodiments of Formula I and/or Formula IA, R³ and R⁴ are independently hydrogen, $C_1$-$C_6$ alkyl, $C_1$-$C_6$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, or R³ and R⁴ taken together represent =CR³'(R⁴'), wherein R³' and R⁴' are independently hydrogen, $C_1$-$C_6$ alkyl, $C_1$-$C_6$ alkoxy, or $C_1$-$C_6$ alkylamino. In some embodiments of Formula I and/or Formula IA, at least one of R³ and R⁴ is hydrogen. In some embodiments of Formula I and/or Formula IA, R³ and R⁴ are both hydrogen.

In some embodiments of Formula I and/or Formula IA, R² is Cl, OMe, vinyl, or 1-propenyl; and R³ and R⁴ are both hydrogen. In some embodiments of Formula I and/or Formula IA, R² is Cl and R³ and R⁴ are both hydrogen. In some embodiments of Formula I and/or Formula IA, R² is OMe and R³ and R⁴ are both hydrogen. In some embodiments of Formula I and/or Formula IA, R² is vinyl or 1-propenyl; and R³ and R⁴ are both hydrogen.

In some embodiments, the compound can be defined by the structure below

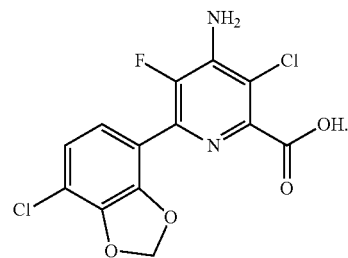 [SMILES: Nc1c(F)c(-c2ccc(Cl)c3c2OCO3)nc(C(=O)O)c1Cl]

In some embodiments, the compound can be defined by the structure below

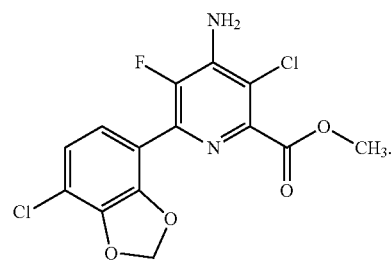 [SMILES: COC(=O)c1nc(-c2ccc(Cl)c3c2OCO3)c(F)c(N)c1Cl]

In some embodiments, the compound can be defined by the structure below

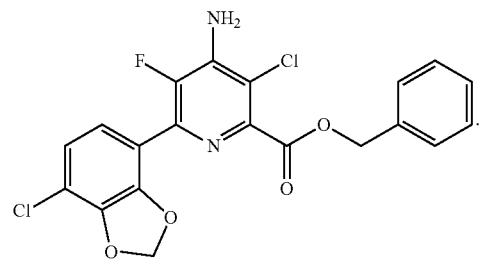 [SMILES: Nc1c(F)c(-c2ccc(Cl)c3c2OCO3)nc(C(=O)OCc2ccccc2)c1Cl]

In some embodiments, the compound can be defined by the structure below

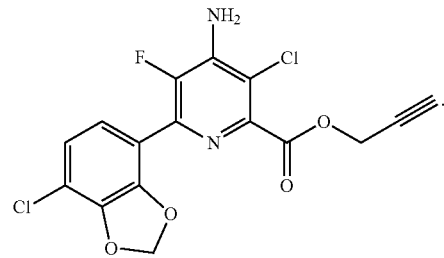 [SMILES: C#CCOC(=O)c1nc(-c2ccc(Cl)c3c2OCO3)c(F)c(N)c1Cl]

Methods of Preparing the Compounds

Exemplary procedures to synthesize the compounds of Formula I and Formula IA are provided below.

As depicted in Scheme I, the 4,5,6-trichloropicolinate of Formula (VII) can be converted to the corresponding isopropyl ester of Formula (VIII), via a reaction with isopropyl alcohol and concentrated sulfuric acid, e.g., at reflux temperature under Dean-Stark conditions (reaction d). The isopropyl ester of Formula (VIII) can be reacted with a fluoride ion source, such as cesium fluoride, in a polar, aprotic solvent, such as dimethyl sulfoxide (DMSO), at a temperature, such as 80° C., under Dean-Stark conditions, to yield the isopropyl 4,5,6-trifluoropicolinate of Formula (IX) (reaction e). The isopropyl 4,5,6-trifluoropicolinate of Formula (IX) can be aminated with a nitrogen source, such as ammonia, in a polar, aprotic solvent, such as DMSO, to produce a 4-amino-5,6-difluoropicolinate of Formula (X) (reaction f). The fluoro substituent in the 6-position of the 4-amino-5,6-difluoropicolinate of Formula (X) can be exchanged with a chloro substituent by treatment with a chloride source, such as hydrogen chloride, e.g., in dioxane, in a Parr reactor, at a temperature, such as 100° C., to produce a 4-amino-5-fluoro-6-chloro-picolinate of Formula (XI) (reaction g). The 4-amino-5-fluoro-6-chloropicolinate of Formula (XI) can be transesterified to the corresponding methyl ester of Formula (XII) by reaction with titanium(IV) isopropoxide in methyl alcohol at reflux temperature (reaction h).

Scheme I

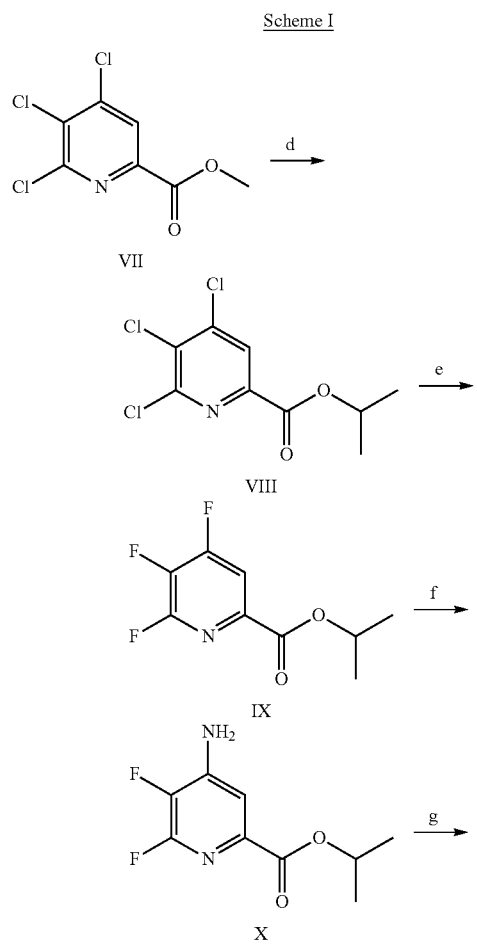

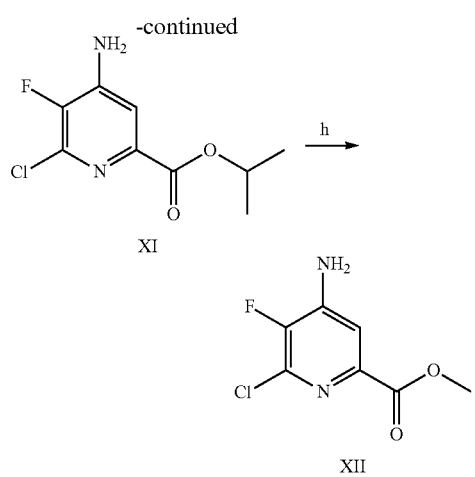

As depicted in Scheme II, the 4-amino-5-fluoro-6-chloropicolinate of Formula (XII) can be transformed into the 3-iodo-4-amino-5-fluoro-6-chloropicolinate of Formula (XIII) via reaction with iodinating reagents, such as periodic acid and iodine, in a polar, protic solvent, such as methyl alcohol (reaction $b_3$). Stille coupling of the 3-iodo-4-amino-5-fluoro-6-chloropicolinates of Formula (XIII) with a stannane, such as tributyl(vinyl)stannane, in the presence of a catalyst, such as bis(triphenylphosphine)-palladium(II) dichloride, in a non-reactive solvent, such as 1,2-dichloroethane, at a temperature, such as 120-130° C., e.g., in a microwave reactor, provides 3-(substituted)-4-amino-5-fluoro-6-chloropicolinates of Formula (XIV), wherein $R^2$ is alkyl, alkenyl, alkynyl, haloalkenyl and alkylthio (reaction $c_3$). Alternatively, the 3-iodo-4-amino-5-fluoro-6-chloropicolinates of Formula (XIII) can be treated with cesium carbonate and a catalytic amount of both copper(I) iodide and 1,10-phenanthroline in the presence of a polar, protic solvent, such as methyl alcohol, at a temperature, such as 65° C., to provide a 3-(substituted)-4-amino-5-fluoro-6-chloropicolinic acids of Formula (XIV), wherein $R^2$ is alkoxy or haloalkoxy (reaction i), which can be esterified to the methyl esters, e.g., by treatment with hydrogen chloride (gas) and methyl alcohol at 50° C. (reaction j). The 3-(substituted)-4-amino-5-fluoro-6-chloropicolinates of Formula (XIV) can be converted to the 4-amino-6-substituted-picolinates of Formula (I-B), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_3$).

Alternatively, the 4-amino-5-fluoro-6-chloropicolinates of Formula (XII) can be converted to the 4-amino-5-fluoro-6-substituted-picolinates of Formula (XV), wherein Ar is as herein defined, via Suzuki coupling with a boronic acid or ester, in the presence of a base, such as potassium fluoride, and a catalyst, such as bis(triphenylphosphine)-palladium (II) dichloride, in a polar, protic solvent mixture, such as acetonitrile-water, at a temperature, such as 110° C., e.g., in a microwave reactor (reaction $a_4$). The 4-amino-5-fluoro-6-substituted-picolinates of Formula (XV) can be transformed into the 3-iodo-4-amino-5-fluoro-6-substituted-picolinates of Formula (XVI) via reaction with iodinating reagents, such as periodic acid and iodine, in a polar, protic solvent, such as methyl alcohol (reaction $b_4$). Stille coupling of the 3-iodo-4-amino-5-fluoro-6-substituted-picolinates of Formula (XVI) with a stannane, such as tributyl(vinyl)stannane, in the presence of a catalyst, such as bis(triphenylphosphine)-palladium(II) dichloride, in a non-reactive solvent, such as 1,2-dichloroethane, at a temperature, such as 120-130° C., e.g., in a microwave reactor, provides 3-(substituted)-4-amino-5-fluoro-6-substituted-picolinates of Formula (I-B), wherein $R^2$ is alkyl, alkenyl, alkynyl, haloalkenyl and alkylthio (reaction $c_4$). Alternatively, the 3-iodo-4-amino-5-fluoro-6-substituted-picolinates of Formula (XVI) can be treated with cesium carbonate and a catalytic amount of both copper(I) iodide and 1,10-phenanthroline in the presence of a polar, protic solvent, such as methyl alcohol, at a temperature, such as 65° C., to provide a 3-(substituted)-4-amino-5-fluoro-6-substituted-picolinic acids of Formula (I-B), wherein $R^2$ is alkoxy or haloalkoxy (reaction $i_2$), which can be esterified to the methyl esters, e.g., by treatment with hydrogen chloride (gas) and methyl alcohol, at a temperature, such as 50° C. (reaction $j_2$).

mula C can be converted to 3-bromo-6-chlorobenzene-1,2-diol of Formula D via a Dakin reaction using an oxidizing agent such as hydrogen peroxide and an aqueous solution of a base such as sodium hydroxide. In step d, 3-bromo-6-chlorobenzene-1,2-diol of Formula D can be converted to 4-bromo-7-chlorobenzo[d][1,3]dioxole of Formula E via an intramolecular cyclisation reaction with a dihalomethane alkylating agent such as bromochloromethane and a base like cesium carbonate in a polar aprotic solvent such a dimethylformamide. In step e, 2-(7-chlorobenzo[d][1,3]dioxol-4-yl)-4,4,5,5-tetramethyl-1,3,2-dioxaborolane of Formula F can be prepared from 4-bromo-7-chlorobenzo[d][1,3]dioxole of Formula E via a halogen/metal exchange reaction using a Grignard reagent such as isopropylmagnesium chloride in a solvent like tetrahydrofuran followed by quenching the organomagnesium intermediate formed in-situ with a borylating agent such as 2-isopropoxy-4,4,5,5-tetramethyl-1,3-dioxalane. In step f, methyl 4-amino-3-chloro-6-(7-chlorobenzo[d][1,3]dioxol-4-yl)-5-fluoropicolinate of Formula H can be prepared via a Suzuki

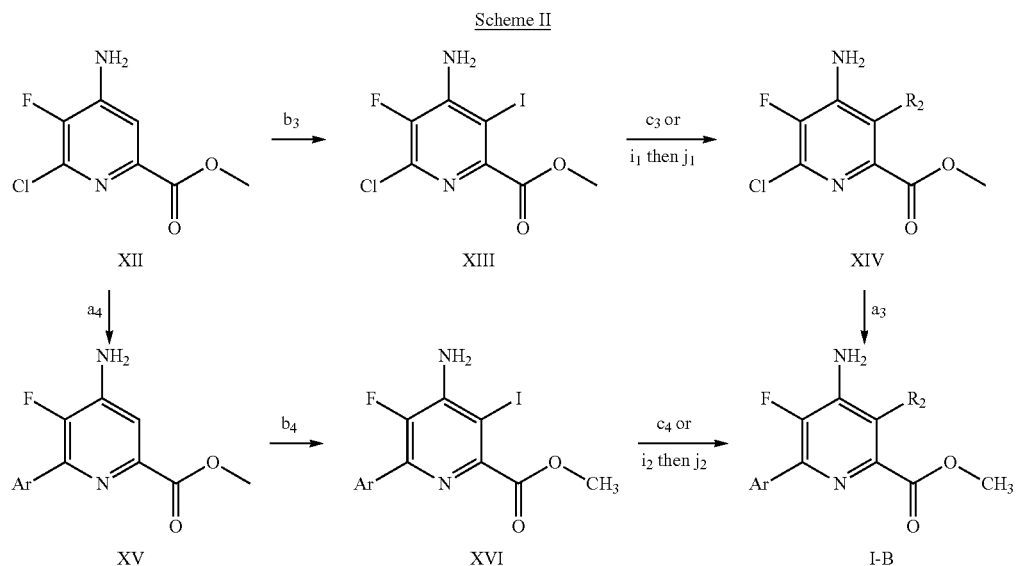

Scheme II

The compounds of I-B obtained by any of these processes, can be recovered by conventional means and purified by standard procedures, such as by recrystallization or chromatography. Many compounds of Formula I and/or IA can be prepared from compounds of Formulae I-B using standard methods well known in the art.

Other compounds of Formula I and/or IA can be prepared using the methods illustrated in Scheme III. In step a of Scheme III, the known 3-bromo-6-chloro-2-fluorobenzaldehyde of Formula A (Balko, T. William et al., International Publication No. WO 2007/082098, which is incorporated herein by reference in its entirety) can be converted to 3-bromo-6-chloro-2-methoxybenzaldehyde of Formula B by substitution nucleophilic aromatic of the 2-fluoro group with a methoxide salt such as sodium methoxide in a solvent like methanol. In step b, 3-bromo-6-chloro-2-methoxybenzaldehyde of Formula B can be converted to 3-bromo-6-chloro-2-hydroxybenzaldehyde of Formula C by demethylation of the 2-methoxy group with a Lewis acid such as boron tribromide in an aprotic solvent like dichloromethane. In step c, 3-bromo-6-chloro-2-hydroxybenzaldehyde of For-coupling between 2-(7-chlorobenzo[d][1,3]dioxol-4-yl)-4,4,5,5-tetramethyl-1,3,2-dioxaborolane of Formula F and known methyl 4-amino-3,6-dichloro-5-fluoropicolinate of Formula G (Fields, Stephen C. et al. Tetrahedron Letters, 51(1), 79-81; 2010) using a palladium (II) catalyst such as bis(triphenylphosphine)palladium(II) dichloride, a base like cesium fluoride in a mixture of solvents such as acetonitrile and water. In step g, methyl 4-amino-3-chloro-6-(7-chlorobenzo[d][1,3]dioxol-4-yl)-5-fluoropicolinate of Formula H can be converted to 4-amino-3-chloro-6-(7-chlorobenzo[d][1,3]dioxol-4-yl)-5-fluoropicolinic acid of Formula I via a saponification reaction using an aqueous solution of a base such as sodium hydroxide in a mixture of solvents like methanol and tetrahydrofuran. In step h, picolinic ester of Formula J can be prepared from 4-amino-3-chloro-6-(7-chlorobenzo[d][1,3]dioxol-4-yl)-5-fluoropicolinic acid via an alkylation reaction using an alkylating agent such as propargyl bromide or benzyl bromide and a base such as potassium carbonate in a polar aprotic solvent like dimethylformamide

Scheme III

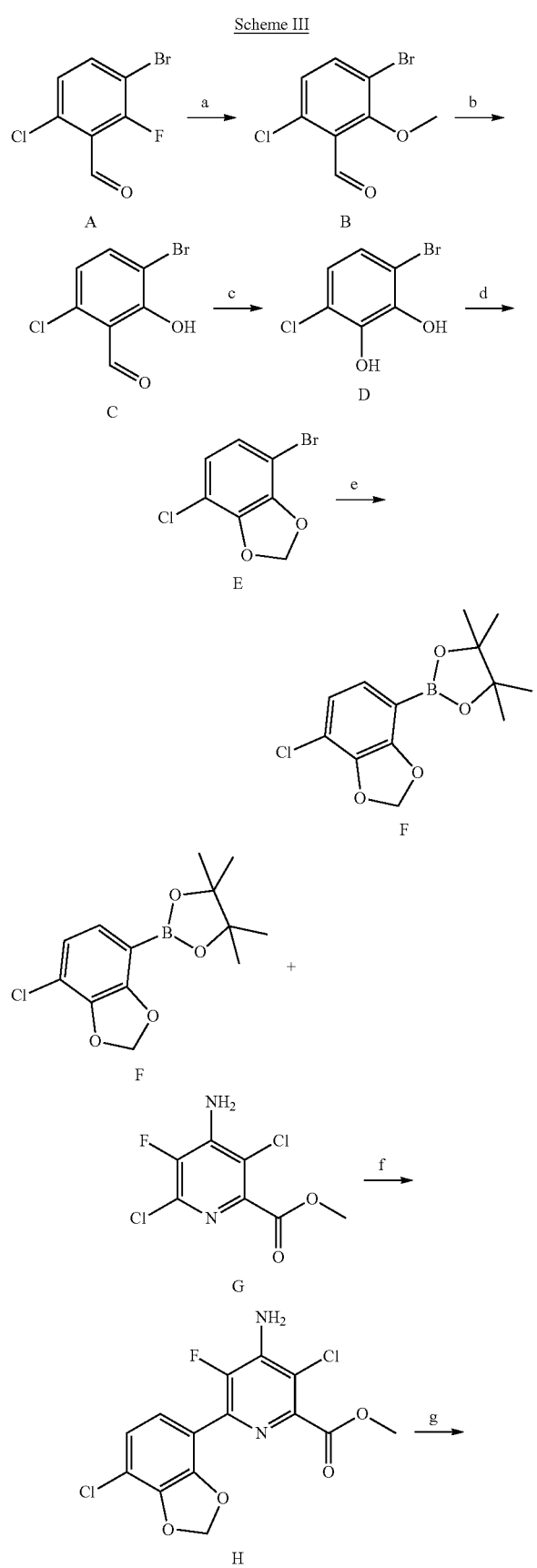
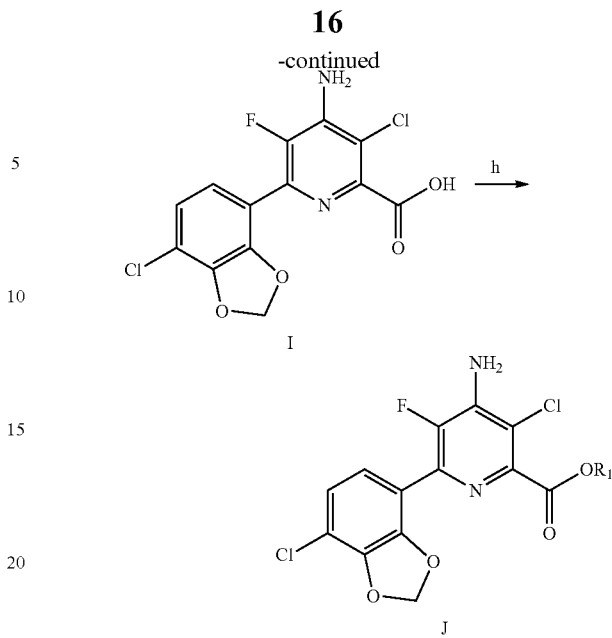

Compositions and Methods

In some embodiments, the compounds provided herein are employed in mixtures containing a herbicidally effective amount of the compound along with at least one agriculturally acceptable adjuvant or carrier. Exemplary adjuvants or carriers include those that are not phytotoxic or significantly phytotoxic to valuable crops, e.g., at the concentrations employed in applying the compositions for selective weed control in the presence of crops, and/or do not react or significantly react chemically with the compounds provided herein or other composition ingredients. Such mixtures can be designed for application directly to weeds or their locus or can be concentrates or formulations that are diluted with additional carriers and adjuvants before application. They can be solids, such as, for example, dusts, granules, water dispersible granules, or wettable powders, or liquids, such as, emulsifiable concentrates, solutions, emulsions or suspensions. They can also be provided as a pre-mix or tank-mixed.

Suitable agricultural adjuvants and carriers that are useful in preparing the herbicidal mixtures of the disclosure are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethylhexyl stearate, n-butyl oleate, isopropyl myristate, propylene glycol dioleate, di-octyl succinate, di-butyl adipate, di-octyl phthalate and the like; esters of mono-, di- and poly-carboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers, and the like. In some embodiments, water is the carrier for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

In some embodiments, one or more surface-active agents are utilized in the compositions of the present disclosure. Such surface-active agents are, in some embodiments, employed in both solid and liquid compositions, e.g., those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in *McCutcheon's Detergents and Emulsifiers Annual*, MC Publishing Corp., Ridgewood, N.J., 1998, and in *Encyclopedia of Surfactants*, Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-Cis ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, e.g., methyl esters.

Oftentimes, some of these materials, such as vegetable or seed oils and their esters, can be used interchangeably as an agricultural adjuvant, as a liquid carrier or as a surface active agent.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this disclosure is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation or flood water, and by other conventional means known to those skilled in the art.

In some embodiments, the compounds and compositions described herein are applied as a post-emergence application, pre-emergence application, in-water application to flooded paddy rice or water bodies (e.g., ponds, lakes and streams), or burn-down application.

In some embodiments, the compounds and compositions provided herein are utilized to control weeds in crops, including but not limited to citrus, apple, rubber, oil, palm, forestry, direct-seeded, water-seeded and transplanted rice, wheat, barley, oats, rye, sorghum, corn/maize, pastures, grasslands, rangelands, fallowland, turf, tree and vine orchards, aquatics, or row-crops, as well as non-crop settings, e.g., industrial vegetation management (IVM) or rights-of-way. In some embodiments, the compounds and compositions are used to control woody plants, broadleaf and grass weeds, or sedges.

In some embodiments, the compounds and compositions provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall panicum, PANDI), *Paspalum dilatatum* Poir. (dallisgrass, PASDI), *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SCPJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq.

(ivyleaf morningglory, IPOHE), *Lindernia dubia* (L.) Pennell (low false pimpernel, LIDDU), *Monochoria korsakowii* Regel & Maack (*monochoria*, MOOKA), *Monochoria vaginalis* (Burm. F.) C. Presl ex Kuhth (*monochoria*, MOOVA), *Murdannia nudiflora* (L.) Brenan (doveweed, MUDNU), *Polygonum pensylvanicum* L. (Pennsylvania smartweed, POLPY), *Polygonum persicaria* L. (ladysthumb, POLPE), *Polygonum hydropiperoides* Michx. (mild smartweed, POLHP), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the compounds and compositions provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POAAN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (*kochia*, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the compounds and compositions provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly *sida*, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the compounds and compositions provided herein are utilized to control undesirable vegetation found in row crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall *panicum*, PANDI), *Panicum miliaceum* L. (wild-proso millet, PANMI), *Setariafaberi Herrm.* (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnfolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly sida, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

In some embodiments, application rates of about 1 to about 4,000 grams/hectare (g/ha) are employed in post-emergence operations. In some embodiments, rates of about 1 to about 4,000 g/ha are employed in pre-emergence operations.

In some embodiments, the compounds, compositions, and methods provided herein are used in conjunction with one or more other herbicides to control a wider variety of undesirable vegetation. When used in conjunction with other herbicides, the presently claimed compounds can be formulated with the other herbicide or herbicides, tank-mixed with the other herbicide or herbicides or applied sequentially with the other herbicide or herbicides. Some of the herbicides that can be employed in conjunction with the compounds of the present disclosure include: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-ammonium, glyphosate, halosafen, halosulfuron-methyl, haloxydine, haloxyfop-methyl, haloxyfop-P-methyl, halauxifen-methyl, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-methyl, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr esters and amines, tridiphane, trietazine, trifloxysulfuron, trifluralin, triflusulfuron, trifop, trifopsime, trihydroxytriazine, trimeturon, tripropindan, tritac, tritosulfuron, vernolate and xylachlor.

The compounds and compositions of the present disclosure can generally be employed in combination with known herbicide safeners, such as benoxacor, benthiocarb, brassinolide, cloquintocet (e.g., mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, R29148 and N-phenylsulfonylbenzoic acid amides, to enhance their selectivity.

The compounds, compositions, and methods described herein be used to control undesirable vegetation on glyphosate-tolerant-, glufosinate-tolerant-, dicamba-tolerant-, phenoxy auxin-tolerant-, pyridyloxy auxin-tolerant-, aryloxyphenoxypropionate-tolerant-, acetyl CoA carboxylase (ACCase) inhibitor-tolerant-, imidazolinone-tolerant-, acetolactate synthase (ALS) inhibitor-tolerant-, 4-hydroxyphenyl-pyruvate dioxygenase (HPPD) inhibitor-tolerant-, protoporphyrinogen oxidase (PPO) inhibitor-tolerant-, triazine-tolerant-, and bromoxynil-tolerant-crops (such as, but not limited to, soybean, cotton, canola/oilseed rape, rice, cereals, corn, turf, etc.), for example, in conjunction with glyphosate, glufosinate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil. The compositions and methods may be used in controlling undesirable vegetation in crops possessing multiple or stacked traits conferring tolerance to multiple chemistries and/or inhibitors of multiple modes-of-action.

The compounds and compositions provided herein may also be employed to control herbicide resistant or tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

Synthesis of Compounds of Formula I

Preparation of Compounds 1, 1A, 1B, and 1C. Synthetic procedures for the preparation of Compounds 1, 1A, 1B, and 1C were prepare as detailed below.

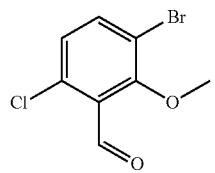

B

To 3-bromo-6-chloro-2-fluorobenzaldehyde A (10 g, 42.1 mmol) (Balko, T. William et al., International Publication No. WO 2007/082098, which is incorporated herein by reference in its entirety) was added 0.5 M sodium methoxide (93 ml, 46.3 mmol). The reaction was heated at 80° C. for 5 h. The reaction was cooled to room temperature overnight. The methanol was removed under vacuum and the slurry was redissolved in ethyl acetate and washed twice with water and once with brine. The organic layer was dried over sodium sulfate, filtered, and concentrated to afford the title compound (9.61 g, 90% yield) as a yellow solid. Mp=73-77° C.; $^1$H NMR (300 MHz, CDCl$_3$) δ 10.41 (s, 1H), 7.68 (d, J=8.6 Hz, 1H), 7.15 (d, J=8.6 Hz, 1H), 3.94 (s, 3H); EIMS m/z 250.

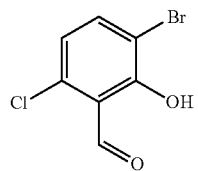

C

To 3-bromo-6-chloro-2-methoxybenzaldehyde B (2.13 g, 8.54 mmol) in dichloromethane (34 mL) at −40° C. was added 1 N boron tribromide (17 mL, 17.00 mmol) over 10 min. After 1.5 h, the reaction was quenched with about 10 mL of acetonitrile and water and stirred for 10 min. Water (50 mL) was then added and the biphasic solution was stirred for 1 h. The organic layer was washed with brine and then filtered through a phase separator and concentrated to provide the title compound (1.97 g, 93% yield) as a yellow solid. Mp 97-106° C.; $^1$H NMR (400 MHz, Chloroform-d) δ 12.57 (s, 1H), 10.37 (s, 1H), 7.69 (dd, J=8.4, 0.5 Hz, 1H), 6.90 (d, J=8.5 Hz, 1H); EIMS m/z 236.

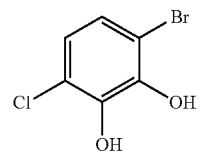

D

A 25-mL vial was charged with 3-bromo-6-chloro-2-hydroxybenzaldehyde C (502 mg, 2.13 mmol) and 1 N sodium hydroxide (2.24 mL, 2.24 mmol) was added. The solid suspension was heated at 50° C. for 5 min. To a vial containing water (3.4 mL) was added 25 wt % hydrogen peroxide (0.34 mL, 2.77 mmol). The hydrogen peroxide solution was added to the heating suspension. The reaction was heated an additional 1 hour, then cooled to room temperature and acidified with 2 N HCl. The solution was extracted with ethyl acetate (twice), dried organic layers over sodium sulfate, filtered, and concentrated to provide the title compound (484 mg, 97% yield) as a brown sticky solid. $^1$H NMR (300 MHz, CDCl$_3$) δ 7.01 (dd, J=8.8, 0.4 Hz, 1H), 6.83 (dd, J=8.8, 0.4 Hz, 1H), 5.67 (s, 2H); $^{13}$C NMR (101 MHz, CDCl$_3$) δ 141.70, 140.51, 123.56, 121.50, 119.45, 107.72; EIMS m/z 224.

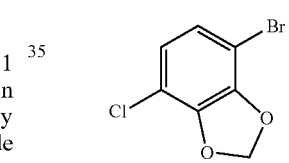

E

A microwave reaction vial was charged with cesium carbonate (840 mg, 2.58 mmol) followed by 3-bromo-6-chlorobenzene-1,2-diol D (480 mg, 2.15 mmol) in DMF (5.4 mL) and bromochloromethane (0.168 mL, 2.58 mmol) via syringe. The reaction mixture was heated in a microwave reactor at 60° C. for 2 h. The reaction mixture was then diluted with ethyl acetate and washed with water. The aqueous layer was extracted with ethyl acetate. The organic layers were washed with water and brine. The combined organic layers were dried over sodium sulfate, filtered, and concentrated, then dried under vacuum to provide the title compound (416 mg, 78% yield) as a brown solid. Mp=92-97° C.; $^1$H NMR (400 MHz, CDCl$_3$) δ 6.92 (d, J=8.9 Hz, 1H), 6.74 (d, J=8.9 Hz, 1H), 6.11 (s, 2H); EIMS m/z 235.

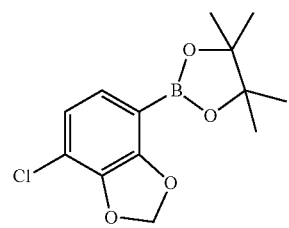

F

4-Bromo-7-chlorobenzo[d][1,3]dioxole E (3.26 g, 13.6 mmol) was stirred in THF (67 mL). The solution was cooled to 0° C. Isopropylmagnesium chloride (8.82 ml, 17.6 mmol) (2 M, Et₂O) was added via syringe over ~10 minutes. The mixture was stirred at 0° C. After 5 h, 2-isopropoxy-4,4,5,5-tetramethyl-1,3-dioxolane (3.72 ml, 17.6 mmol) was added dropwise via syringe over ~5 minutes. The mixture was stirred and allowed to warm to room temperature. After 22 h, the mixture was poured into saturated NH₄Cl (50 mL). The mixture was extracted with EtOAc (200 mL). The extract was washed with brine (50 mL), dried over Na₂SO₄, filtered and concentrated to provide the title compound (3.96 g, 98% yield) as a light yellow solid. Mp=116-118° C.; ¹H NMR (400 MHz, Chloroform-d) δ 7.15 (d, J=8.4 Hz, 1H), 6.82 (d, J=8.4 Hz, 1H), 6.09 (s, 2H), 1.35 (s, 12H); EIMS m/z 282.

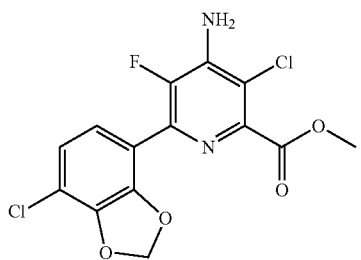

1A

To a nitrogen purged solution of 2-(7-chlorobenzo[d][1,3]dioxol-4-yl)-4,4,5,5-tetramethyl-1,3,2-dioxaborolane F (17.73 g, 62.8 mmol), methyl 4-amino-3,6-dichloro-5-fluoropicolinate G (10 g, 41.8 mmol) (Fields, Stephen C. et al. Tetrahedron Letters, 51(1), 79-81; 2010; which is incorporated herein by reference in its entirety) and cesium fluoride (19.07 g, 126 mmol) in CH₃CN (76 mL) and water (20 mL) was added Pd(PPh₃)₂Cl₂ (2.94 g, 4.18 mmol). The mixture was purged with N₂ for 10 min while the solids were dissolved and then heated at reflux for 4 h. Upon cooling the mixture to room temperature, the product crystallized. The mixture was filtered and the solid was washed with acetonitrile. The filtrate was concentrated to remove most of the acetonitrile, diluted with water and extracted with ethyl acetate. The ethyl acetate extracts were combined, washed with brine, dried over MgSO₄ and concentrated under reduced pressure to give an orange solid. To this solid was added acetone. This mixture was filtered and the solid was washed with ether and combined with the 1st crop to give the title compound (13 g, 85% yield) as a yellow solid. Mp=198-200° C.; ¹H NMR (400 MHz, Chloroform-d) δ 7.10 (dd, J=8.7, 0.6 Hz, 1H), 6.95 (d, J=8.7 Hz, 1H), 6.10 (s, 2H), 4.91 (s, 2H), 3.98 (s, 3H); ¹⁹F NMR (376 MHz, CDCl₃) δ−137.59; ESIMS m/z 360 [(M+H)⁺].

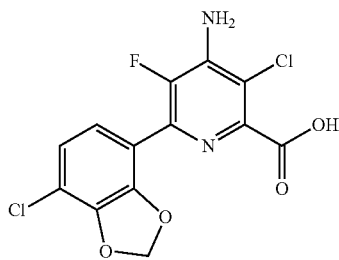

1

To methyl 4-amino-3-chloro-6-(7-chlorobenzo[d][1,3]dioxol-4-yl)-5-fluoropicolinate 1A (158 mg, 0.440 mmol) in methanol (2.20 mL) was added 2 N sodium hydroxide (440 µl, 0.88 mmol). The reaction was acidified with 2 N HCl and the methanol was blown off under a stream of nitrogen. The solid was vacuum filtered, rinsed with water, and dried in a vacuum oven to provide the title compound (137 mg, 88% yield) as a white solid. Mp 200-201° C.; ¹H NMR (400 MHz, DMSO-d₆) δ 13.62 (s, 1H), 7.06 (s, 2H), 6.95 (s, 2H), 6.20 (s, 2H); ¹⁹F NMR (376 MHz, DMSO-d₆) δ−137.72; ESIMS m/z 345 ([M+H]⁺).

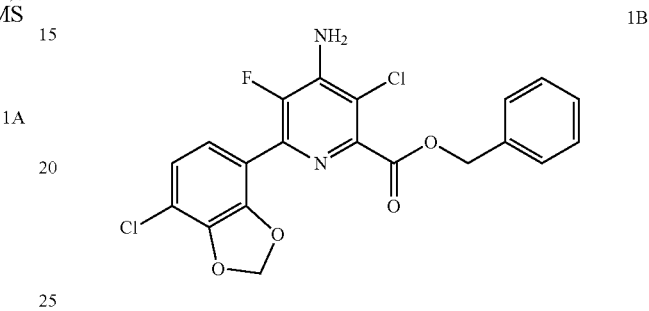

1B

To 4-amino-3-chloro-6-(7-chlorobenzo[d][1,3]dioxol-4-yl)-5-fluoropicolinic acid 1 (102 mg, 0.296 mmol) and potassium carbonate (56 mg, 0.405 mmol) in DMF (0.985 mL) was added benzyl bromide (0.042 mL, 0.355 mmol) and the reaction was heated at 60° C. for 4 h. The reaction mixture was directly loaded onto a celite cartridge with acetonitrile and dried in the vacuum oven overnight. The crude product was purified by reversed phase preparative HPLC (acetonitrile/water gradient) to afford the title compound (89 mg, 69% yield) as a white solid. Mp 155-157° C.; ¹H NMR (400 MHz, CDCl₃) 7.49-7.43 (m, 2H), 7.42-7.33 (m, 3H), 7.12 (d, J=8.7 Hz, 1H), 6.94 (d, J=8.7 Hz, 1H), 6.09 (s, 2H), 5.43 (s, 2H), 4.88 (s, 2H); ¹⁹F NMR (376 MHz, CDCl₃) δ−137.76; ESIMS m/z 435 ([M+H]⁺).

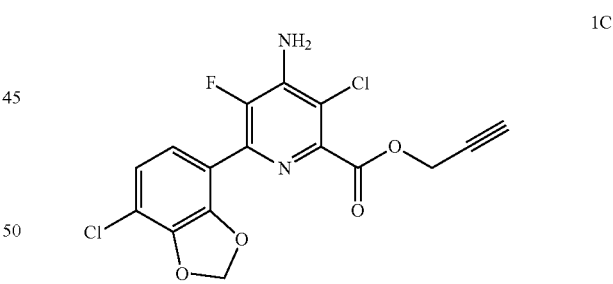

1C

To 4-amino-3-chloro-6-(7-chlorobenzo[d][1,3]dioxol-4-yl)-5-fluoropicolinic acid 1 (105 mg, 0.304 mmol) and potassium carbonate (75 mg, 0.543 mmol) in DMF (0.985 mL) was added 3-bromoprop-1-yne (0.039 mL, 0.365 mmol) and the reaction was heated at 60° C. The reaction mixture was directly loaded onto a celite cartridge with acetonitrile and dried in the vacuum oven overnight. The crude product was purified by reversed phase preparative HPLC (acetonitrile/water gradient) to afford the title compound (63 mg, 54% yield) as a tan solid. Mp 163-168° C.; ¹H NMR (400 MHz, CDCl₃) δ 7.12 (d, J=8.6 Hz, 1H), 6.95 (d, J=8.7 Hz, 1H), 6.10 (s, 2H), 4.97 (d, J=2.5 Hz, 2H), 4.92 (s, 2H), 2.53 (t, J=2.5 Hz, 1H); ¹⁹F NMR (376 MHz, CDCl3) δ−137.10; ESIMS m/z 383 ([M+H]⁺)

Compounds 2-15 were prepared as described in U.S. Pat. No. 9,149,038, which is incorporated herein by reference in its entirety.

The structure of Compounds 1-15 are shown in the Table below.

| Compound No. | Structure |
|---|---|
| 1 | 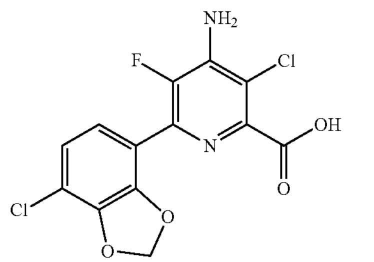 [SMILES: Nc1c(F)c(-c2ccc(Cl)c3c2OCO3)nc(C(=O)O)c1Cl] |
| 1A | 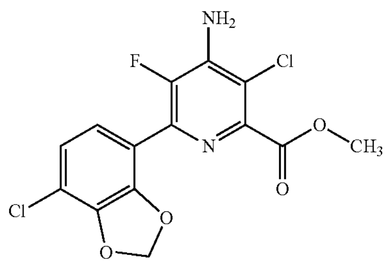 [SMILES: COC(=O)c1nc(-c2ccc(Cl)c3c2OCO3)c(F)c(N)c1Cl] |
| 1B | 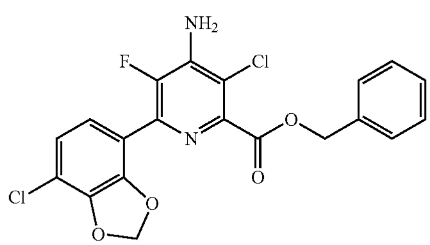 [SMILES: Nc1c(F)c(-c2ccc(Cl)c3c2OCO3)nc(C(=O)OCc2ccccc2)c1Cl] |
| 1C | 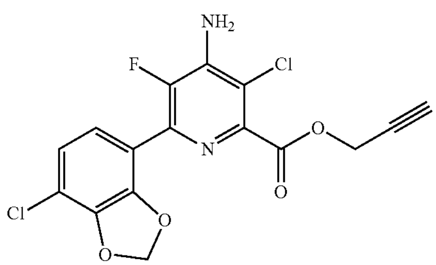 [SMILES: C#CCOC(=O)c1nc(-c2ccc(Cl)c3c2OCO3)c(F)c(N)c1Cl] |
| 2 | 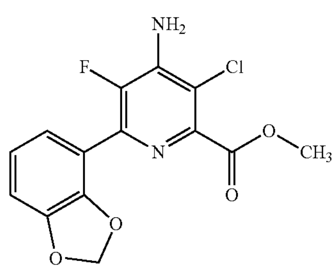 [SMILES: COC(=O)c1nc(-c2cccc3c2OCO3)c(F)c(N)c1Cl] |

-continued

| Compound No. | Structure |
|---|---|
| 3 | 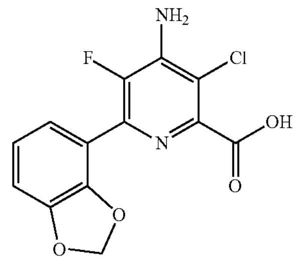 [SMILES: Nc1c(F)c(-c2cccc3c2OCO3)nc(C(=O)O)c1Cl] |
| 4 | 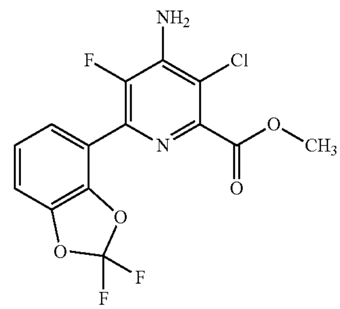 [SMILES: COC(=O)c1nc(-c2cccc3c2OC(F)(F)O3)c(F)c(N)c1Cl] |
| 5 | 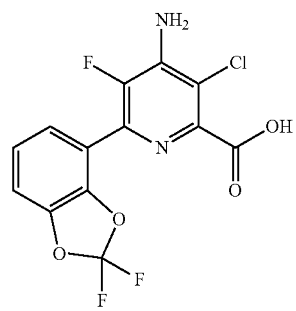 [SMILES: Nc1c(F)c(-c2cccc3c2OC(F)(F)O3)nc(C(=O)O)c1Cl] |
| 6 | 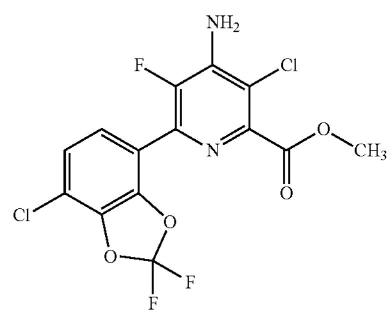 [SMILES: COC(=O)c1nc(-c2ccc(Cl)c3c2OC(F)(F)O3)c(F)c(N)c1Cl] |
| 7 | 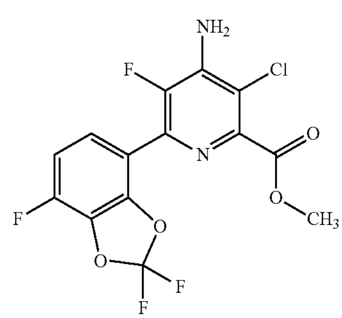 [SMILES: COC(=O)c1nc(-c2ccc(F)c3c2OC(F)(F)O3)c(F)c(N)c1Cl] |

| Compound No. | Structure |
|---|---|
| 8 | 4-amino-3-chloro-5-fluoro-6-(7-fluoro-2,2-difluoro-1,3-benzodioxol-4-yl)pyridine-2-carboxylic acid |
| 9 | methyl 4-amino-3-chloro-5-fluoro-6-(7-bromo-2,2-difluoro-1,3-benzodioxol-4-yl)pyridine-2-carboxylate |
| 10 | methyl 4-amino-3-chloro-5-fluoro-6-(7-iodo-2,2-difluoro-1,3-benzodioxol-4-yl)pyridine-2-carboxylate |
| 11 | 4-amino-3-chloro-5-fluoro-6-(7-bromo-2,2-difluoro-1,3-benzodioxol-4-yl)pyridine-2-carboxylic acid |
| 12 | 4-amino-3-chloro-5-fluoro-6-(7-iodo-2,2-difluoro-1,3-benzodioxol-4-yl)pyridine-2-carboxylic acid |
| 13 | methyl 4-amino-3,5-dichloro-6-(7-chloro-2,2-difluoro-1,3-benzodioxol-4-yl)pyridine-2-carboxylate |
| 14 | 4-amino-3-chloro-5-fluoro-6-(7-chloro-2,2-difluoro-1,3-benzodioxol-4-yl)pyridine-2-carboxylic acid |
| 15 | methyl 4-amino-3-chloro-5-fluoro-6-(7-fluoro-1,3-benzodioxol-4-yl)pyridine-2-carboxylate |

EXAMPLES

Example 1. Evaluation of Herbicidal Activity

Post-Emergent Test: Seeds or nutlets of the desired test plant species were planted in Sun Gro Metro-Mix® 360 planting mixture, which typically has a pH of 6.0 to 6.8 and an organic matter content of about 30 percent, in plastic pots with a surface area of 64 square centimeters ($cm^2$). When required to ensure good germination and healthy plants, a fungicide treatment and/or other chemical or physical treatment was applied. The plants were grown for 7-21 d in a greenhouse with an approximate 15 h photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 mL glass vial and was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of a 97:3 v/v mixture of acetone and DMSO and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain ½×, ¼×, ⅛× and ¹⁄₁₆× rates of the high rate. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by subirrigation to prevent wash-off of the test compounds. After 14 d, the condition of the test plants as compared with that of the untreated plants was determined visually and scored on a scale of 0 to 100 percent where 0 corresponds to no injury and 100 corresponds to complete kill.

Figure 1B:
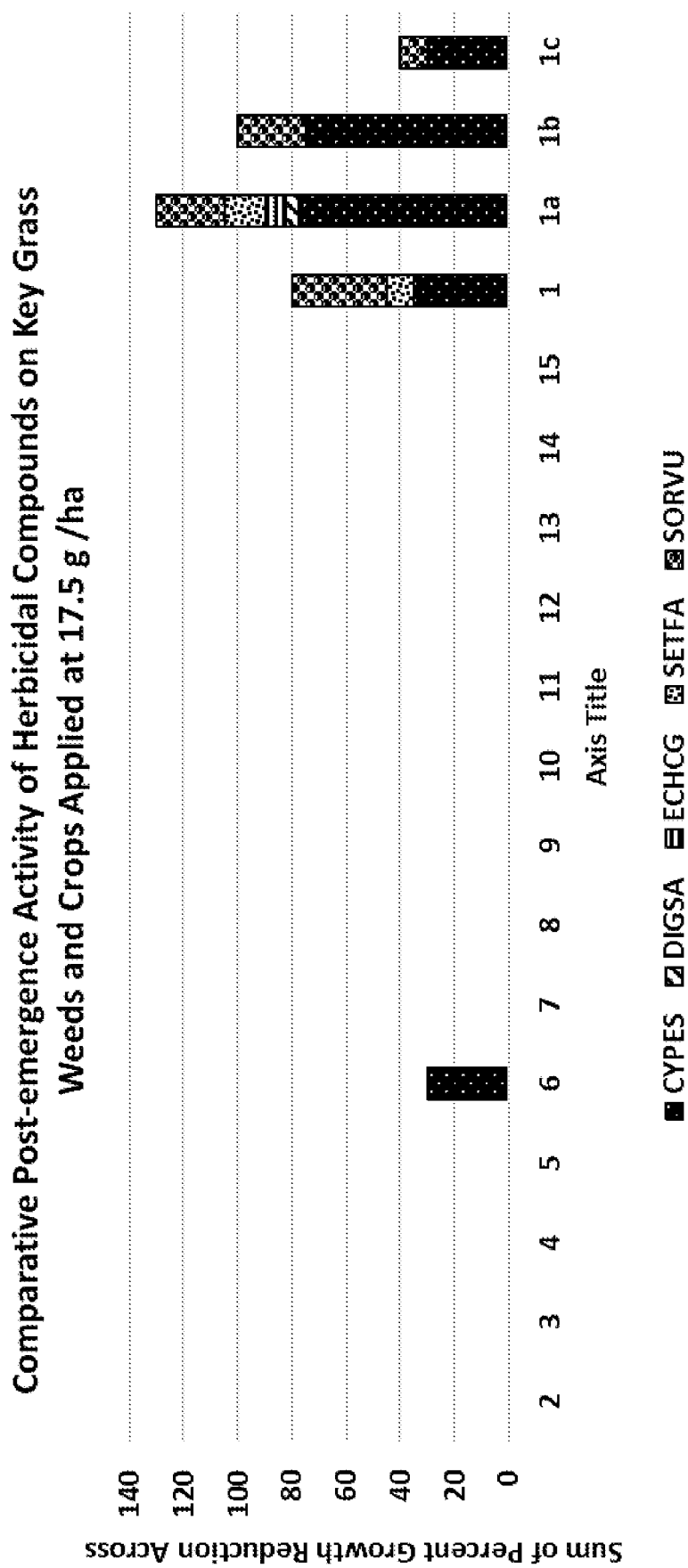
FIG. 1B is a plot of the activity of Compounds 1-15 against selected grass weed species at an application rate of 17.5 g ai/ha.
Figure 2A:
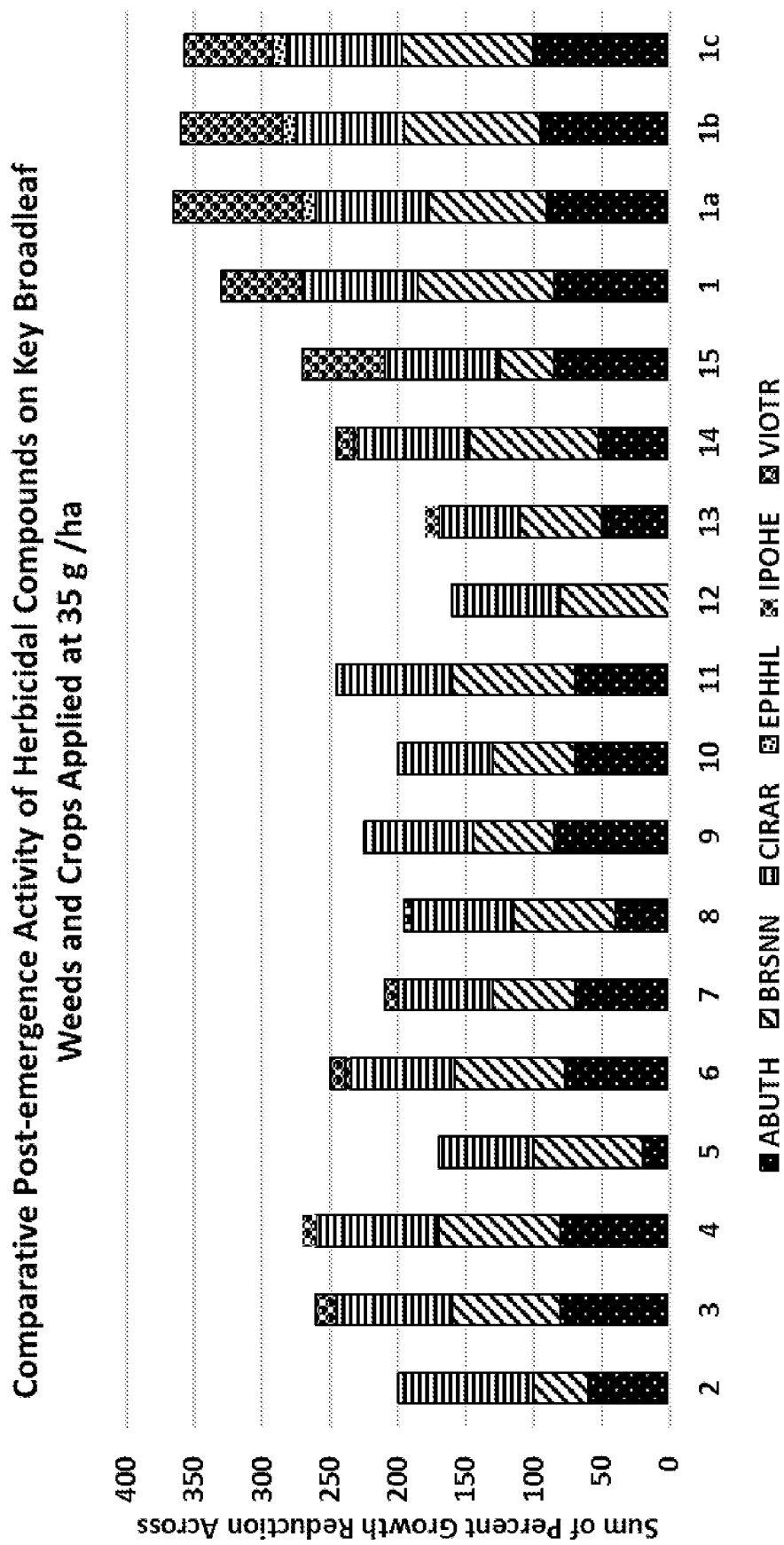
FIG. 2A is a plot of the activity of Compounds 1-15 against selected broadleaf weed species at an application rate of 35 g ai/ha.
Figure 2B:
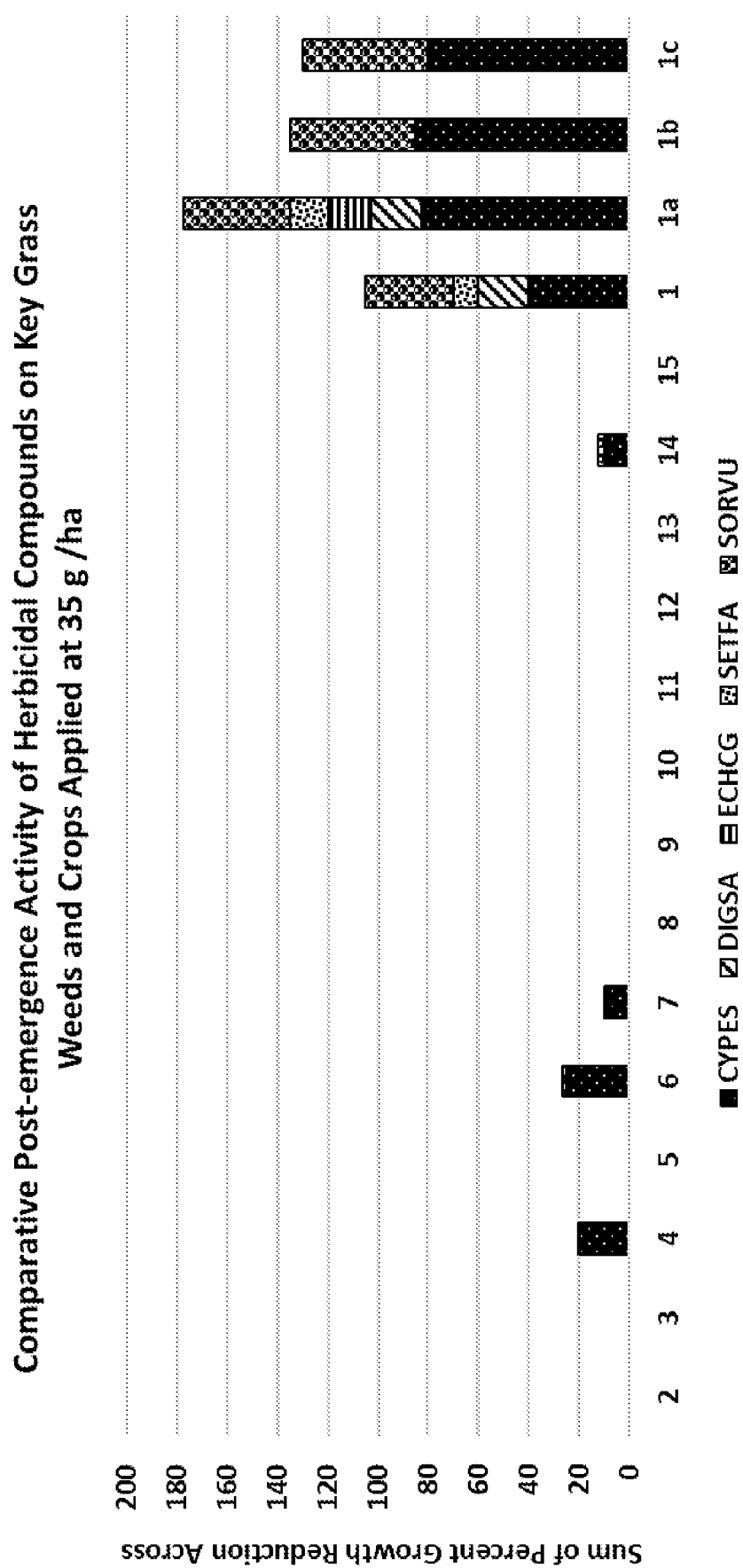
FIG. 2B is a plot of the activity of Compounds 1-15 against selected grass weed species at an application rate of 35 g ai/ha.
Figure 3A:
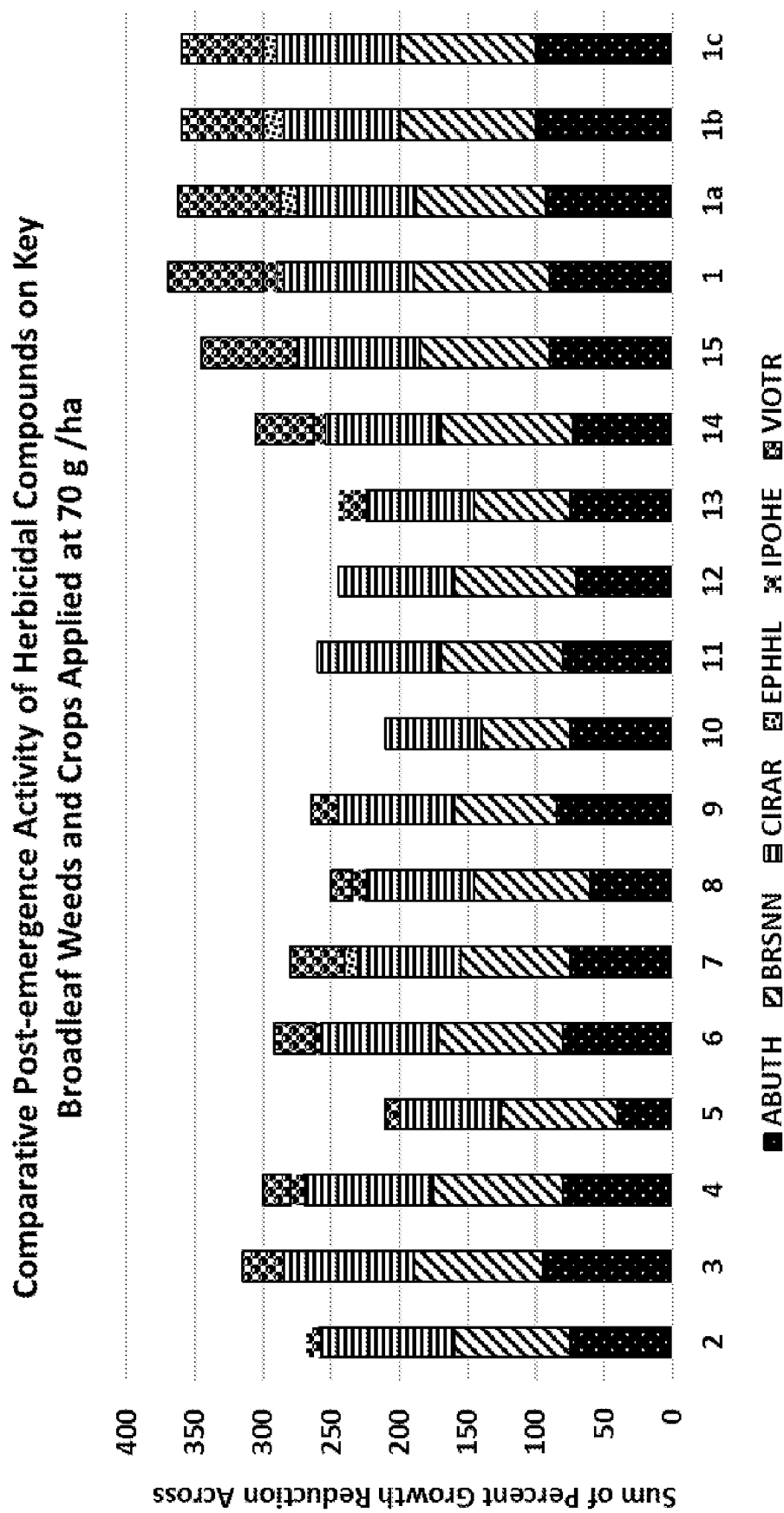
FIG. 3A is a plot of the activity of Compounds 1-15 against selected broadleaf weed species at an application rate of 70 g ai/ha.
Figure 3B:
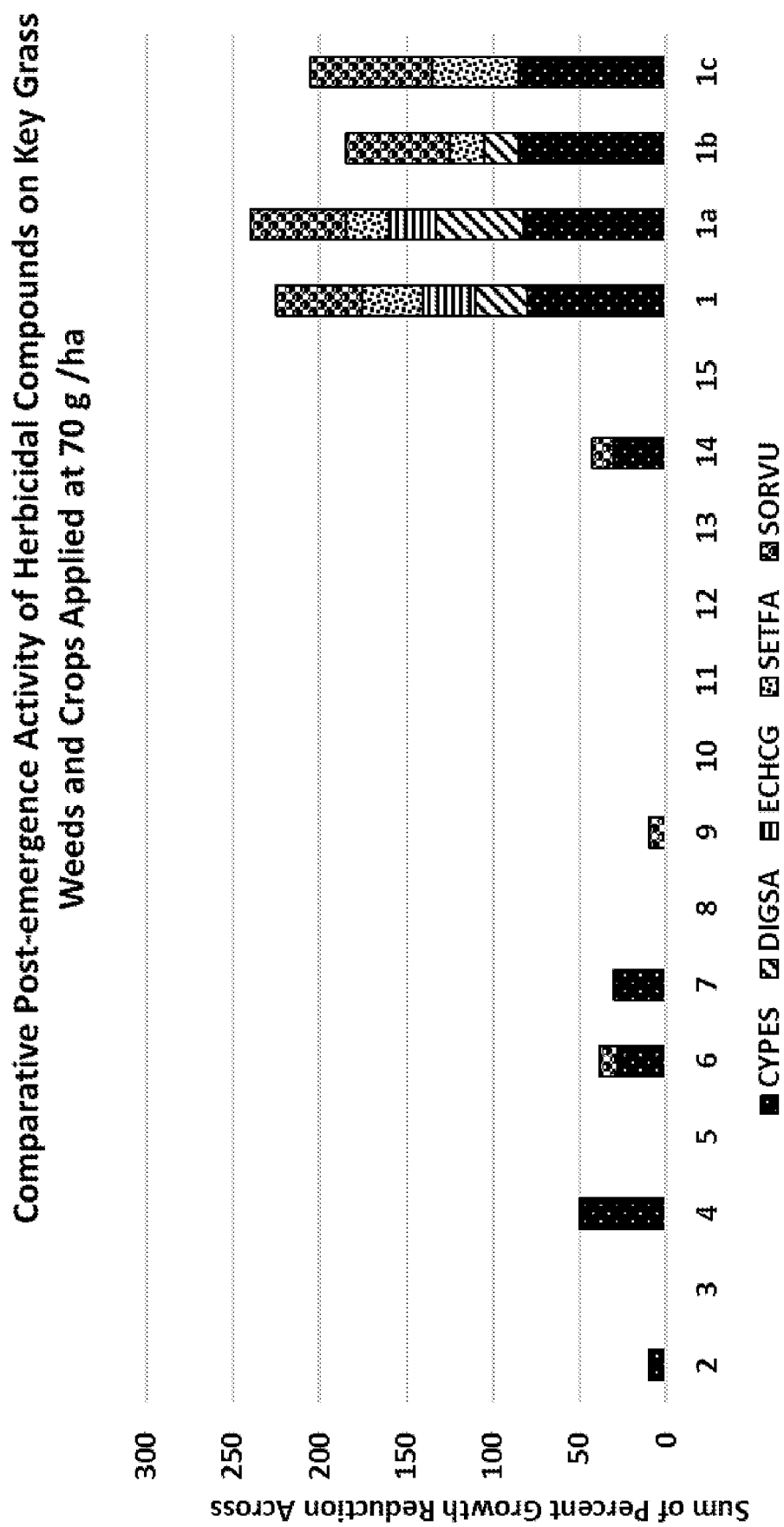
FIG. 3B is a plot of the activity of Compounds 1-15 against selected grass weed species at an application rate of 70 g ai/ha.
Figure 4A:
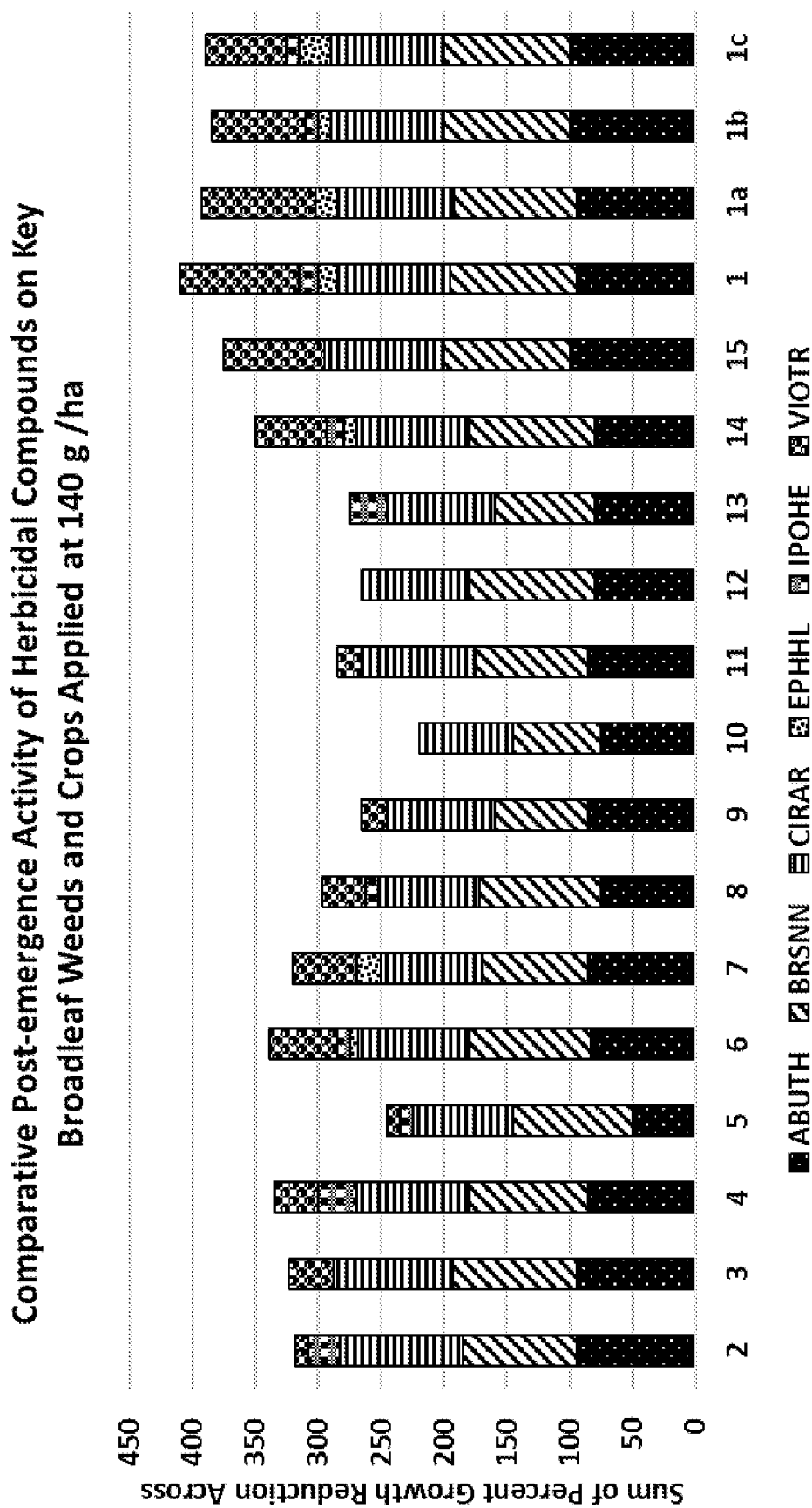
FIG. 4A is a plot of the activity of Compounds 1-15 against selected broadleaf weed species at an application rate of 140 g ai/ha.
Figure 4B:
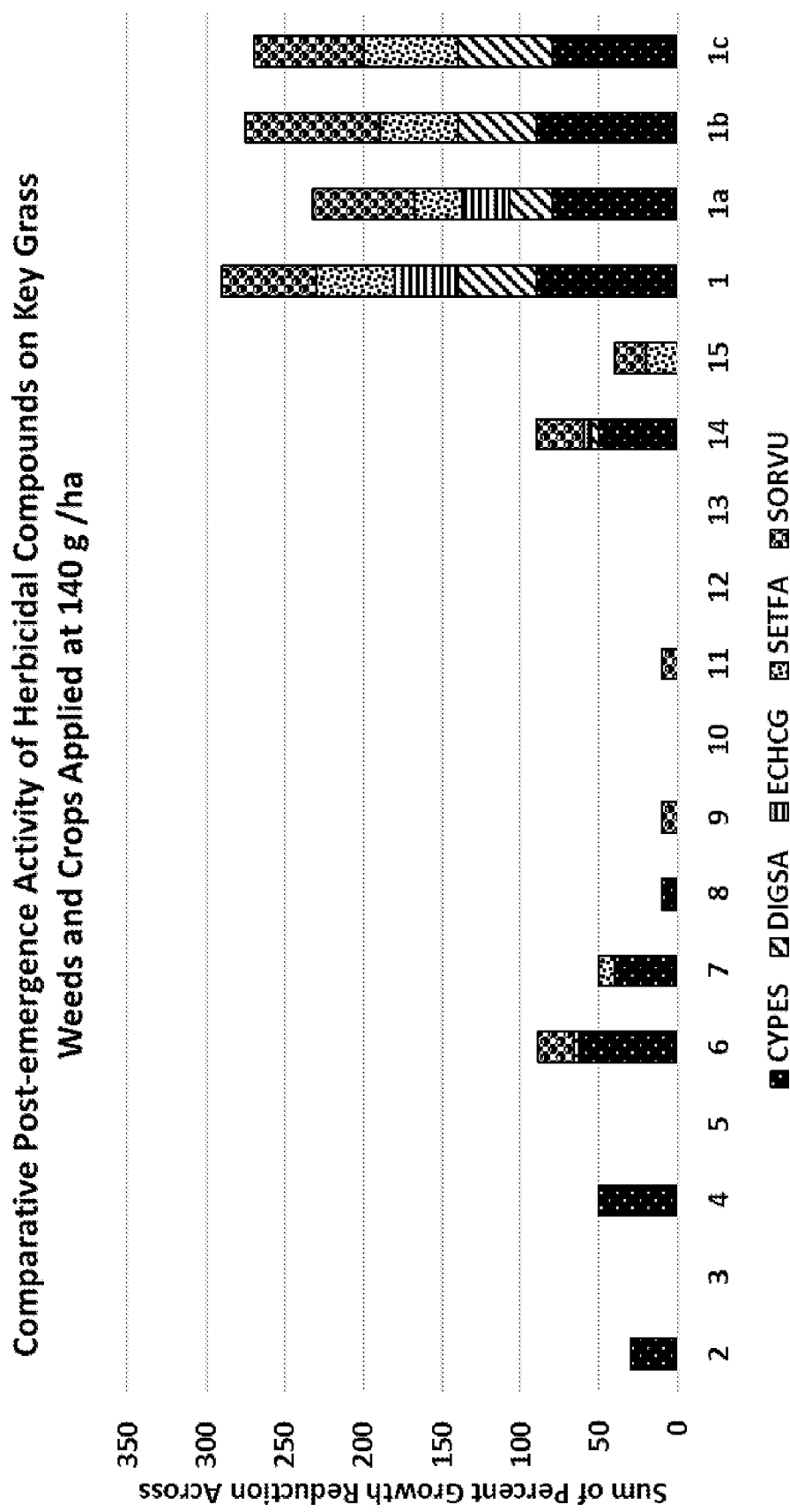
FIG. 4B is a plot of the activity of Compounds 1-15 against selected grass weed species at an application rate of 140 g ai/ha.

Some of the compounds tested, application rates employed, plant species tested, and results are given in Tables 1 and 2. These results are also plotted in FIGS. 1A-4B. As shown in Tables 1-2 and FIGS. 1A-4B, compounds of Formula I (e.g., Compound 1) exhibit significantly improved herbicidal activity as compared to a number of structurally similar compounds (e.g., Compounds 2-15). The improved activity of compounds of Formula I (e.g., Compound 1) as compared to a number of structurally similar compounds (e.g., Compounds 2-15) was unexpected.

TABLE 1

Post-Emergent Herbicidal Activity of Compounds 1-15 on Key Broadleaf Weed Species

| C. No. | Application Rate (g ai/ha) | Visual Growth Reduction (%) 14 Days After Application | | | | | |
|---|---|---|---|---|---|---|---|
| | | ABUTH | BRSNN | CIRAR | EPHHL | IPOHE | VIOTR |
| 1 | 17.5 | 80 | 55 | 85 | 0 | 0 | 40 |
| | 35 | 85 | 100 | 85 | 0 | 0 | 60 |
| | 70 | 90 | 100 | 95 | 5 | 10 | 70 |
| | 140 | 95 | 100 | 90 | 15 | 15 | 95 |
| 1A | 17.5 | 85 | 78 | 83 | 3 | 0 | 53 |
| | 35 | 90 | 88 | 83 | 10 | 0 | 95 |
| | 70 | 93 | 95 | 88 | 13 | 0 | 75 |
| | 140 | 95 | 98 | 93 | 18 | 0 | 90 |
| 1B | 17.5 | 90 | 95 | 75 | 10 | 0 | 40 |
| | 35 | 95 | 100 | 80 | 10 | 0 | 75 |
| | 70 | 100 | 100 | 85 | 15 | 0 | 60 |
| | 140 | 100 | 100 | 90 | 10 | 10 | 75 |
| 1C | 17.5 | 100 | 95 | 70 | 10 | 0 | 65 |
| | 35 | 100 | 97 | 85 | 10 | 0 | 65 |
| | 70 | 100 | 100 | 90 | 10 | 0 | 60 |
| | 140 | 100 | 100 | 90 | 25 | 10 | 65 |
| 2 | 17.5 | 50 | 30 | 60 | 0 | 0 | 0 |
| | 35 | 60 | 40 | 100 | 0 | 0 | 0 |
| | 70 | 75 | 85 | 98 | 0 | 10 | 0 |
| | 140 | 95 | 90 | 98 | 0 | 25 | 10 |
| 3 | 17.5 | 60 | 60 | 70 | 0 | 0 | 0 |
| | 35 | 80 | 80 | 85 | 0 | 0 | 15 |
| | 70 | 95 | 95 | 95 | 0 | 0 | 30 |
| | 140 | 95 | 98 | 95 | 0 | 0 | 35 |
| 4 | 17.5 | 70 | 85 | 80 | 0 | 0 | 0 |
| | 35 | 80 | 90 | 90 | 0 | 10 | 0 |
| | 70 | 80 | 95 | 95 | 0 | 10 | 20 |
| | 140 | 85 | 95 | 90 | 0 | 30 | 35 |
| 5 | 17.5 | 10 | 75 | 60 | 0 | 0 | 0 |
| | 35 | 20 | 80 | 70 | 0 | 0 | 0 |
| | 70 | 40 | 85 | 75 | 0 | 0 | 10 |
| | 140 | 50 | 95 | 80 | 0 | 10 | 10 |
| 6 | 17.5 | 75 | 80 | 70 | 2 | 0 | 3 |
| | 35 | 77 | 82 | 77 | 0 | 3 | 12 |
| | 70 | 80 | 92 | 85 | 2 | 3 | 30 |
| | 140 | 83 | 97 | 88 | 7 | 10 | 53 |
| 7 | 17.5 | 50 | 50 | 60 | 0 | 0 | 5 |
| | 35 | 70 | 60 | 70 | 0 | 0 | 10 |
| | 70 | 75 | 80 | 75 | 10 | 0 | 40 |
| | 140 | 85 | 85 | 80 | 20 | 0 | 50 |
| 8 | 17.5 | 30 | 70 | 20 | 0 | 0 | 0 |
| | 35 | 40 | 75 | 75 | 0 | 0 | 5 |
| | 70 | 60 | 85 | 80 | 0 | 10 | 15 |
| | 140 | 75 | 97 | 80 | 0 | 10 | 35 |
| 9 | 17.5 | 80 | 60 | 70 | 0 | 0 | 0 |
| | 35 | 85 | 60 | 80 | 0 | 0 | 0 |
| | 70 | 85 | 75 | 85 | 0 | 0 | 20 |
| | 140 | 85 | 75 | 85 | 0 | 0 | 20 |

TABLE 1-continued

Post-Emergent Herbicidal Activity of Compounds 1-15 on Key Broadleaf Weed Species

| C. No. | Application Rate (g ai/ha) | ABUTH | BRSNN | CIRAR | EPHHL | IPOHE | VIOTR |
|---|---|---|---|---|---|---|---|
| 10 | 17.5 | 65 | 50 | 60 | 0 | 0 | 0 |
|  | 35 | 70 | 60 | 70 | 0 | 0 | 0 |
|  | 70 | 75 | 65 | 70 | 0 | 0 | 0 |
|  | 140 | 75 | 70 | 75 | 0 | 0 | 0 |
| 11 | 17.5 | 50 | 90 | 80 | 0 | 0 | 0 |
|  | 35 | 70 | 90 | 85 | 0 | 0 | 0 |
|  | 70 | 80 | 90 | 90 | 0 | 0 | 0 |
|  | 140 | 85 | 90 | 90 | 0 | 0 | 20 |
| 12 | 17.5 | 0 | 70 | 65 | 0 | 0 | 0 |
|  | 35 | 0 | 80 | 80 | 0 | 0 | 0 |
|  | 70 | 70 | 90 | 85 | 0 | 0 | 0 |
|  | 140 | 80 | 100 | 85 | 0 | 0 | 0 |
| 13 | 17.5 | 30 | 40 | 50 | 0 | 0 | 0 |
|  | 35 | 50 | 60 | 60 | 0 | 10 | 0 |
|  | 70 | 75 | 70 | 80 | 0 | 20 | 0 |
|  | 140 | 80 | 80 | 85 | 0 | 30 | 0 |
| 14 | 17.5 | 43 | 90 | 78 | 0 | 3 | 5 |
|  | 35 | 53 | 95 | 83 | 0 | 3 | 13 |
|  | 70 | 73 | 98 | 85 | 0 | 8 | 43 |
|  | 140 | 80 | 100 | 90 | 10 | 13 | 58 |
| 15 | 17.5 | 70 | 20 | 80 | 0 | 0 | 30 |
|  | 35 | 85 | 40 | 85 | 0 | 0 | 60 |
|  | 70 | 90 | 95 | 90 | 0 | 0 | 70 |
|  | 140 | 100 | 100 | 95 | 0 | 0 | 80 |

ABUTH: velvetleaf (*Abutilon theophrasti*)
BRSNN: oilseed rape, canola (*Brassica napus*)
CIRAR: Canada thistle (*Cirsium arvense*)
EPHHL: wild poinsettia (*Euphorbia heterophylla*)
IPOHE: ivyleaf morningglory (*Ipomoea hederacea*)
VIOTR: wild violet (*Viola tricolor*)
g ai/ha: grams active ingredient per hectare
n/t: not tested

TABLE 2

Post-Emergent Herbicidal Activity of Compounds 1-15 on Key Grass Weed Species

| C. No. | Application Rate (g ai/ha) | CYPES | DIGSA | ECHCG | SETFA | SORVU |
|---|---|---|---|---|---|---|
| 1 | 17.5 | 35 | 0 | 0 | 10 | 35 |
|  | 35 | 40 | 20 | 0 | 10 | 35 |
|  | 70 | 80 | 30 | 30 | 35 | 50 |
|  | 140 | 90 | 50 | 40 | 50 | 60 |
| 1A | 17.5 | 78 | 5 | 8 | 15 | 25 |
|  | 35 | 83 | 20 | 18 | 15 | 43 |
|  | 70 | 83 | 50 | 28 | 25 | 55 |
|  | 140 | 80 | 28 | 30 | 30 | 65 |
| 1B | 17.5 | 75 | 0 | 0 | 0 | 25 |
|  | 35 | 85 | 0 | 0 | 0 | 50 |
|  | 70 | 85 | 20 | 0 | 20 | 60 |
|  | 140 | 90 | 50 | 0 | 50 | 85 |
| 1C | 17.5 | 30 | 0 | 0 | 0 | 10 |
|  | 35 | 80 | 0 | 0 | 0 | 50 |
|  | 70 | 85 | 0 | 0 | 50 | 70 |
|  | 140 | 80 | 60 | 0 | 60 | 70 |
| 2 | 17.5 | 0 | 0 | 0 | 0 | 0 |
|  | 35 | 0 | 0 | 0 | 0 | 0 |
|  | 70 | 10 | 0 | 0 | 0 | 0 |
|  | 140 | 30 | 0 | 0 | 0 | 0 |
| 3 | 17.5 | 0 | 0 | 0 | 0 | 0 |
|  | 35 | 0 | 0 | 0 | 0 | 0 |
|  | 70 | 0 | 0 | 0 | 0 | 0 |
|  | 140 | 0 | 0 | 0 | 0 | 0 |
| 4 | 17.5 | 0 | 0 | 0 | 0 | 0 |
|  | 35 | 20 | 0 | 0 | 0 | 0 |
|  | 70 | 50 | 0 | 0 | 0 | 0 |
|  | 140 | 50 | 0 | 0 | 0 | 0 |
| 5 | 17.5 | 0 | 0 | 0 | 0 | 0 |
|  | 35 | 0 | 0 | 0 | 0 | 0 |
|  | 70 | 0 | 0 | 0 | 0 | 0 |
|  | 140 | 0 | 0 | 0 | 0 | 0 |
| 6 | 17.5 | 30 | 0 | 0 | 0 | 0 |
|  | 35 | 25 | 0 | 0 | 0 | 2 |
|  | 70 | 25 | 0 | 3 | 0 | 10 |
|  | 140 | 60 | 0 | 3 | 3 | 23 |
| 7 | 17.5 | 0 | 0 | 0 | 0 | 0 |
|  | 35 | 10 | 0 | 0 | 0 | 0 |
|  | 70 | 30 | 0 | 0 | 0 | 0 |
|  | 140 | 40 | 0 | 0 | 10 | 0 |
| 8 | 17.5 | 0 | 0 | 0 | 0 | 0 |
|  | 35 | 0 | 0 | 0 | 0 | 0 |
|  | 70 | 0 | 0 | 0 | 0 | 0 |
|  | 140 | 10 | 0 | 0 | 0 | 0 |
| 9 | 17.5 | 0 | 0 | 0 | 0 | 0 |
|  | 35 | 0 | 0 | 0 | 0 | 0 |
|  | 70 | 0 | 0 | 0 | 0 | 10 |
|  | 140 | 0 | 0 | 0 | 0 | 10 |

TABLE 2-continued

Post-Emergent Herbicidal Activity of Compounds 1-15 on Key Grass Weed Species

| C. No. | Application Rate (g ai/ha) | CYPES | DIGSA | ECHCG | SETFA | SORVU |
|---|---|---|---|---|---|---|
| 10 | 17.5 | 0 | 0 | 0 | 0 | 0 |
|  | 35 | 0 | 0 | 0 | 0 | 0 |
|  | 70 | 0 | 0 | 0 | 0 | 0 |
|  | 140 | 0 | 0 | 0 | 0 | 0 |
| 11 | 17.5 | 0 | 0 | 0 | 0 | 0 |
|  | 35 | 0 | 0 | 0 | 0 | 0 |
|  | 70 | 0 | 0 | 0 | 0 | 0 |
|  | 140 | 0 | 0 | 0 | 0 | 10 |
| 12 | 17.5 | 0 | 0 | 0 | 0 | 0 |
|  | 35 | 0 | 0 | 0 | 0 | 0 |
|  | 70 | 0 | 0 | 0 | 0 | 0 |
|  | 140 | 0 | 0 | 0 | 0 | 0 |
| 13 | 17.5 | 0 | 0 | 0 | 0 | 0 |
|  | 35 | 0 | 0 | 0 | 0 | 0 |
|  | 70 | 0 | 0 | 0 | 0 | 0 |
|  | 140 | 0 | 0 | 0 | 0 | 0 |
| 14 | 17.5 | 0 | 0 | 0 | 0 | 0 |
|  | 35 | 10 | 0 | 0 | 0 | 3 |
|  | 70 | 30 | 0 | 0 | 0 | 13 |
|  | 140 | 50 | 5 | 5 | 0 | 30 |
| 15 | 17.5 | 0 | 0 | 0 | 0 | 0 |
|  | 35 | 0 | 0 | 0 | 0 | 0 |
|  | 70 | 0 | 0 | 0 | 0 | 0 |
|  | 140 | 0 | 0 | 0 | 20 | 20 |

CYPES: yellow nutsedge (*Cyperus esculentus*)
DIGSA: large crabgrass (*Digitaria sanguinalis*)
ECHCG: barnyardgrass (*Echinochloa crus-galli*)
SETFA: giant foxtail (*Setaria faberi*)
SORVU: shattercane (*Sorghum bicolor*)
g ai/ha: grams active ingredient per hectare
n't: not tested

What is claimed is:

1. A compound defined by Formula I:

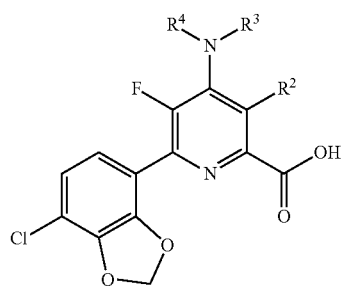

wherein

R² is halogen, $C_1$-$C_4$ alkyl, $C_2$-$C_4$ alkenyl, $C_2$-$C_4$ haloalkenyl, or $C_1$-$C_4$ alkoxy; and R³ and R⁴ are independently hydrogen, $C_1$-$C_6$ alkyl, or formyl;

or an agriculturally acceptable salt, ester, or N-oxide thereof wherein the compound defined by Formula I has improved herbicidal activity as compared to the following compound:

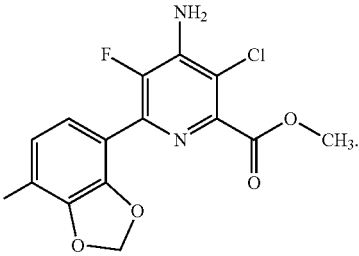

2. The compound of claim 1, wherein the compound is defined by Formula IA:

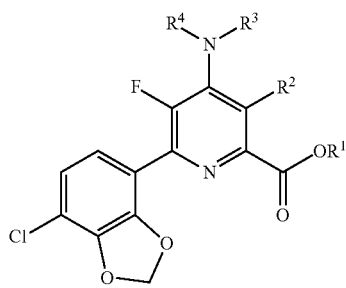

wherein

R¹ is hydrogen, $C_1$-$C_8$ alkyl, $C_1$-$C_8$ haloalkyl, $C_2$-$C_8$ alkenyl, $C_2$-$C_8$ haloalkenyl, $C_2$-$C_8$ alkynyl, phenyl, substituted phenyl, or $C_7$-$C_{12}$ arylalkyl;

R² is halogen, $C_1$-$C_4$ alkyl, $C_2$-$C_4$ alkenyl, or $C_1$-$C_4$ alkoxy; and R³ and R⁴ are independently hydrogen, $C_1$-$C_6$ alkyl, or formyl:

or an agriculturally acceptable salt or N-oxide thereof.

3. The compound of claim 1, wherein R² is halogen, $C_2$-$C_4$-alkenyl, or $C_1$-$C_4$-alkoxy.

4. The compound of claim 1, wherein R² is Cl, methoxy, vinyl, or 1-propenyl.

5. The compound of claim 1, wherein R² is Cl.

6. The compound of claim 1, wherein R³ and R⁴ are both hydrogen.

7. The compound of claim 1, wherein the compound is defined by the structure below

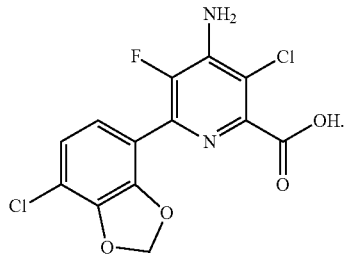 [SMILES: Nc1c(F)c(-c2ccc(Cl)c3c2OCO3)nc(C(=O)O)c1Cl]

8. The compound of claim 1, wherein the compound is defined by the structure below

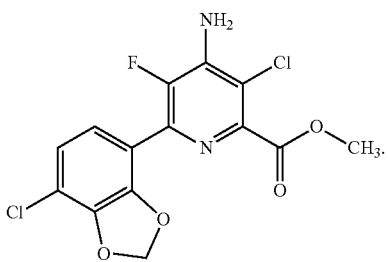

9. The compound of claim 1, wherein the compound is defined by the structure below

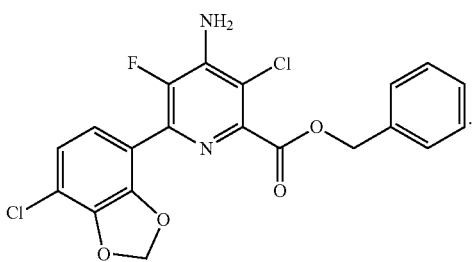 [SMILES: Nc1c(F)c(-c2ccc(Cl)c3c2OCO3)nc(C(=O)OCc2ccccc2)c1Cl]

10. The compound of claim 1, wherein the compound is defined by the structure below

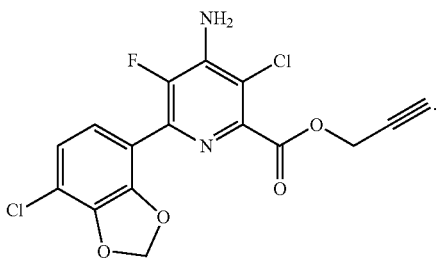 [SMILES: C#CCOC(=O)c1nc(-c2ccc(Cl)c3c2OCO3)c(F)c(N)c1Cl]

11. A herbicidal composition comprising the compound of claim 1 and an agriculturally acceptable adjuvant or carrier, wherein the compound of claim 1 is a herbicide.

12. The composition of claim 11, further comprising at least one additional herbicidal compound.

13. The composition of claim 11, further comprising a safener.

14. A herbicidal composition comprising the compound of claim 7 and an agriculturally acceptable adjuvant or carrier.

15. A herbicidal composition comprising the compound of claim 8 and an agriculturally acceptable adjuvant or carrier.

16. A herbicidal composition comprising the compound of claim 9 and an agriculturally acceptable adjuvant or carrier.

17. A herbicidal composition comprising the compound of claim 10 and an agriculturally acceptable adjuvant or carrier.

18. A method for controlling undesirable vegetation comprising applying a herbicidally effective amount of a compound of claim 1 directed to the undesirable vegetation, or to an area adjacent to the undesirable vegetation, or to an area where control of undesirable vegetation is desired, or to soil or water.

19. A method for controlling undesirable vegetation comprising applying a herbicidally effective amount of the composition of claim 11 directed to the undesirable vegetation, or to an area adjacent to the undesirable vegetation, or to an area where control of undesirable vegetation is desired, or to soil or water.

20. A method for controlling undesirable vegetation comprising applying a herbicidally effective amount of the composition of claim 13 directed to the undesirable vegetation, or to an area adjacent to the undesirable vegetation, or to an area where control of undesirable vegetation is desired, or to soil or water.

* * * * *